(12) United States Patent
Bergmann

(10) Patent No.: US 7,622,262 B2
(45) Date of Patent: Nov. 24, 2009

(54) METHOD FOR DIAGNOSING NEOPLASMS

(75) Inventor: Andreas Bergmann, Berlin (DE)

(73) Assignee: B.R.A.H.M.S. Aktiengesellschaft, Hennigsdorf (DE)

(*) Notice: Subject to any disclaimer, the term of this patent is extended or adjusted under 35 U.S.C. 154(b) by 0 days.

(21) Appl. No.: 10/512,935

(22) PCT Filed: Apr. 4, 2003

(86) PCT No.: PCT/EP03/03552

§ 371 (c)(1),
(2), (4) Date: Jul. 29, 2005

(87) PCT Pub. No.: WO03/093825

PCT Pub. Date: Nov. 13, 2003

(65) Prior Publication Data

US 2006/0051817 A1   Mar. 9, 2006

(30) Foreign Application Priority Data

May 2, 2002 (EP) .................................. 02009884

(51) Int. Cl.
G01N 33/53 (2006.01)
(52) U.S. Cl. ........................ 435/7.1; 435/7.94
(58) Field of Classification Search .................. None
See application file for complete search history.

(56) References Cited

U.S. PATENT DOCUMENTS

| | | | |
|---|---|---|---|
| 4,433,060 A * | 2/1984 | Frenzel | 436/518 |
| 4,593,091 A | 6/1986 | della Valle et al. | |
| 4,831,021 A | 5/1989 | Tubaro et al. | |
| 5,443,952 A * | 8/1995 | Pestronk | 435/7.1 |
| 5,639,617 A | 6/1997 | Bouhoun | |
| 6,756,483 B1 | 6/2004 | Bergmann et al. | |
| 2002/0136735 A1 | 9/2002 | Molina et al. | |

FOREIGN PATENT DOCUMENTS

| | | |
|---|---|---|
| DE | 4227454 | 2/1994 |
| DE | 19847690 | 4/2000 |
| EP | 0656121 | 4/1998 |
| WO | 93/17691 | 9/1993 |
| WO | 99/15201 | 4/1999 |
| WO | 99/40433 | 8/1999 |
| WO | 00/22439 | 4/2000 |
| WO | 01/10877 | 5/2001 |
| WO | 02/17770 | 3/2002 |
| WO | 02/18950 | 3/2002 |

OTHER PUBLICATIONS

Marcus D., Ann Neur 1990, 27:S53-S55.*
Tockman et al, Cancer Res., 1992, 52:2711s-2718s.*
Nishiyama et al, Neuromuscular Disorders, 1993, 3:227-229.*
Doxmorov, I.M. et al., "Nanomolar Concentrations of Gangliosides Stimulate Primary Humoral Response", Biochemistry and Molecular Biology International, vol. 42, No. 1, Jun. 1997, pp. 57-63.
Ryan, John L. et al., "Possible Role for Glycosphingolipids in the Control of Immune Responses", Eur. J. Immunology, 1979, vol. 9, pp. 171-175.
Ledeen, Robert W. et al., "The Role of $GM_1$ and Other Gangliosides in Neuronal Differentiation: Overview and New Findings", Annals of New York Academy of Sciences, 1998, pp. 161-175.
Hakamori, Sen-itiroh et al., "Functional Role of Glycosphingolipids in Cell Recognition and Signaling", Journal of Biochemistry, 1995, vol. 118, pp. 1091-1103.
Yates, Allan J. et al., "Ganglioside Modulation of the PDGF Receptor", Journal of Neuro-Oncology, 1995, vol. 24, pp. 65-73.
Singh, Anup K. et al., "Gangliosides as Receptors for Biological Toxins: Development of Sensitive Fluoroimmunoassays Using Ganglioside-Bearing Liposomes", Analytical Chemistry, 2000, vol. 72, No. 24, pp. 6019-6024.
Krivan, Howard C. et al., "Many Pulmonary Pathogenic Bacteria Bind Specifically to the Carbohydrate Sequence Ga1NAcβ1-4Gal found in some Glycolipids", Proc. Natl. Acad. Sci. USA, Aug. 1988, vol. 85, pp. 6157-6161.
Bäckström, Malin et al., "Characterization of an Internal Permissive Site in the Cholera Toxin B-subunit and Insertion of Epitopes from Human Immunodeficiency Virus-1, Hepatitis B Virus and Enterotoxigenic *Escherichia coli*", Gene, 1995, vol. 165, pp. 163-171.
Lencer, Wayne I. et al., "Membrane Traffic and the Cellular Uptake of Cholera Toxin" Biochemica et Biophysica Acta 1450, 1999, pp. 177-190.
Ratner, Adam J. et al., "Cystic Fibrosis Pathogens Activate $Ca^{2+}$-dependent Mitogen-Activated Protein Kinase Signaling Pathways in Airway Epithelial Cells", Journal of Biological Chemistry, 2001, vol. 276, No. 22, pp. 19267-19275.
Quarles, Richard H. et al., "Autoantibodies Associated with Peripheral Neuropathy", Muscle & Nerve, Jul. 1999, vol. 22, pp. 800-822.
Isoardo, G. et al., "Anti GM1 and Anti-Sulfatide Antibodies in Polyneuropathies", Acta Neural Scand, 2001, vol. 103, pp. 180-187.
Press, Rayomond et al., "Temporal Profile of Anti-Ganglioside Antibodies and Their Relation to Clinical Parameters and Treatment in Guillain-Barré Syndrome", Journal of the Neurological Sciences, 2001, vol. 190, pp. 41-47.
Adams, D. et al., "Predictive Value of Anti GM, Ganglioside Antibodies in Neuromuscular Diseases: A Study of 180 Sera", Journal of Neuroimmunology, 1991, vol. 32, pp. 223-230.

(Continued)

*Primary Examiner*—Misook Yu
*Assistant Examiner*—Mark Halvorson
(74) *Attorney, Agent, or Firm*—Heslin Rothenberg Farley & Mesiti P.C.

(57) ABSTRACT

Disclosed are uses of Gangliosides $G_{M1}$ and/or asialo-$G_{M1}$ substances simulating the carbohydrate portion of said gangliosides with regard to bonding to anti-$G_{M1}$ antibodies and/or anti-$AD_{M1}$ antibodies for producing agents which bind or block anti-$G_{M1}$ antibodies and/or anti-$AG_{M1}$ antibodies which bond to natural killer cells (NKC) or for blocking antigen-presenting cells and producing a T-cell anergy, and for producing an affinity material for the extracorporeal removal of anti-$G_{M1}$ antibodies and/or anti-$AG_{M1}$ antibodies in order to prevent, inhibit, and treat malignant cancers.

3 Claims, 10 Drawing Sheets

OTHER PUBLICATIONS

Yuki, Nobuhiro et al., "Cross-Reactive Antigen Between Nervous Tissue and a Bacterium Elicits Guillain-Barré Syndrome: Molecular Mimicry Between Ganglioside $GM_1$ and Lipopolysaccharide from Penner's Serotype 19 of *Campylobacter jejuni*", Biomedical Research, 1992, vol. 13, No. 6, pp. 451-453.

Schwerer, B. et al., "Antibody Cross-Reactivities Between Gangliosides and Lipopolysaccharides of *Campylobacter jejuni* Serotypes Associated with Guillain-Barré Syndrome", Journal of Endotoxin Research, 1995, vol. 2, pp. 395-403.

Bersudsky, Marina et al., "Lipopolysaccharides of a *Campylobacter coli* Isolate from a Patient with Guillain-Barré Syndrome Display Ganglioside Mimicry", Neuromuscular Disorders, 2000, vol. 10, pp. 182-186.

Prendergast, Martina et al., "Lipopolysaccharides in the Development of the Guillain-Barré Syndrome and Miller Fischer Syndrome Forms of Acute Inflammatory Peripheral Neuropathies", Journal of Endotoxin Research, 2000, vol. 6, No. 5, pp. 341-359.

Neisser, Andrea et al., "Serum Antibodies Against Gangliosides and *Campylobacter jejuni* Lipopolysaccharides in Miller Fischer Syndrome", Infection and Immunity, 1997, vol. 65, No. 10, pp. 4038-4042.

Koga, Michiaki et al, "Close Association of IgA Anti-Ganglioside Antibodies with Antecedent *Campylobacter coli* Infection in Guillain-Barré and Fischer's Syndromes", Journal of Neuroimmunology, 1998, vol. 81, pp. 138-143.

Koga, Michiaki et al., "Subclass Distribution and the Secretory Component of Serum IgA Anti-Ganglioside Antibodies in Guillain-Barré Syndrome after *Campylobacter jejuni* Enteritis", Journal of Neuroimmunology, 1999, vol. 96, pp. 245-250.

Mori, M. et al., "*Haemophilus influenzae* Infection and Guillain-Barré Syndrome", Brain, 2000, vol. 123, pp. 2171-2178.

Nevo, Yoram et al., "Acute Immune Polyneuropathies: Correlations of Serum Antibodies to *Campopylobacter jejuni* and *Helicobacter pylori* with Anti-$GM_1$ Antibodies and Clinical Patterns of Disease", The Journal of Infectious Diseases, 1997, vol. 176, Suppl 2, pp. S154-S156.

McAlarney, T. et al., "Specificity and Cross-Reactivity of Anti-Galactocerebroside Antibodies", Immunological Investigations, 1995, vol. 24, No. 4, pp. 595-606.

Ang, C.W. et al., "Guillain-Barré Syndrome- and Miller Fischer Syndrome-Associated *Campopylobacter jejuni* Lipopolysaccharides Induce Anti-$GM_1$ and Anti-$GQ_{1b}$ Antibodies in Rabbits", Infection and Immunity 2001, vol. 69, No. 4, pp. 2462-2469.

Petratos, Steven et al., "Antibodies Against Peripheral Myelin Glycolipids in People with HIV Infection", Immunology and Cell Biology, 1998, vol. 76, pp. 535-541.

Gisslen, M. et al., "Cerebrospinal Fluid Antibodies Directed Against Neuron-Associated Gangliosides in HIV-1 Infection" Infection 28, 2000, No. 3, pp. 143-148.

Müller, C. et al., "Characterization of Autoantibodies to Natural Killer Cells in HIV-Infected Patients", Scand. J. Immunol, 1996, vol. 43, pp. 583-592.

Adler, Grazyna et al., "Small Cell Lung Cancer is not Asscoiated with the Presence of Anti-Fucosyl-$GM_1$ Ganglioside Autoantibodies Reactive in Immunoenzymatic Test", Lung Cancer, vol. 34, 2001, pp. 383-385.

Lewartowska, Aleksandra et al., "Ganglioside Reactive Antibodies of IgG and IgM Class in Sera of Patients with Differential Thyroid Cancer", Immunology Letters, 2002, vol. 80, No. 2, pp. 129-132.

Konstandoulakis, Manousos M. et al., "Autoantibodies in the Serum of Patients with Gastric Cancer: Their Prognostic Importance", Hybridoma, 1998, vol. 17, No. 5, pp. 431-435.

Nilsson, Olle, "Carbohydrate Antigens in Human Lung Carcinomas", APMIS Suppl. 27, 1992, vol. 100, pp. 149-164.

Weller, Michael et al., "Ganglioside Antibodies: A Lack of Clinical Utility?", Jorunal of Neurology, 1992, vol. 239, pp. 455-459.

McCombe, P.A. et al., "Results of Testing for Anti-$GM_1$ Antibodies", Journal of Clinical Neuroscience, 2000, vol. 7, No. 3, pp. 209-212.

Bech, Einar et al., "ELISA-Type Titertray Assay of IgM Anti-$GM_1$ Autoantibodies", Clinical Chemistry, 1994, vol. 40, No. 7, pp. 1331-1334.

Pestronk, Alan et al., "Multifocal Motor Neuropathy: Serum IgM Anti-GM1 Ganglioside Antibodies in Most Patients Detected Using Covalent Linkage of GM1 to ELISA Plates", Neurology, 1997, vol. 49, pp. 1289-1292.

Ravindranath, Mephur et al., "Factors Affecting to the Fine Specificity and Sensitivity of Serum Antiganglioside Antibodies in ELISA", Journal of Immunological Methods, 1994, vol. 169, pp. 257-272.

Alaedini, Armin et al, "Detection of Anti-GM1 Ganglioside Antibodies in Patients with Neuropathy by a Novel Latex Agglutination Assay", Journal of Immunoassay, 2000, vol. 21, No. 4, pp. 377-386.

Alaedini, Armin et al., "Ganglioside Agglutination Immunoassay for Rapid Detection of Autoantibodies in Immune-Mediated Neuropathy", Journal of Clinical Laboratory Analysis, 2001, vol. 15, pp. 96-99.

Escande-Beillard, Nathalie et al., "A Sensitive Flow Cytometry Method for Anti-GM1 Antibodies Detection", Journal of Neuroimmunology, 2002, vol. 125, pp. 163-169.

International Search Report issued Jun. 25, 2003 in PCT/EP0303553.

Byers, T. (CA Journal, vol. 49(6), Nov./Dec. 1999).

Weller, M. et al., "Ganglioside antibodies: a lack of diagnostic specificity and clinical utility?", Journal of Neurology, vol. 239, 1992, 455-459.

Maysinger et al., "Effects of treatment with microencapsulated monosialoganglioside GM1 on cortical and striatal acetylcholine release in rats with cortical devascularizing lesions", Neuroscience Letters, vol. 118 (1990) 252-256.

Garber, K., Protein C may be sepsis solution, Nature Biotechnology, vol. 18, Sep. 2000, 917-918.

Granziero et al., (Eur. J. Immunol. 1999, 29: 1127-1138).

Endo et al., "Antibodies to glycosphingolipids in patients with multimple sclerosis and SLE", 132(4): 1984.

Redl et al. World J Surg 1996, 20: 487-492.

Standen et al. N Engl J Med 2000, 343: 447-448.

Ogino et al., "IgG anti-GM1 antibodies from patients with acute motor neuropathy are predominantly of the IgG1 and IgG3 subclasses", J. Neuroimmunol. 58:77-80, 1995.

International Search Report from PCT/EP03/03449 mailed Jun. 25, 2003.

Lanier, Lewis L., "NK Cell Receptors", Annu, Rev. Ummunol., vol. 16, 1998, 359-393.

International Search Report from PCT/EP2003/003448 issued Jun. 17, 2003.

Alaniz et al., "Normally Occurring Human Anti-GM1 Immunoglobulin M Antibodies and the Immune Response to Bacteria", Infec. and Immun. 72(4): 2148-2151, 2004.

Heremans et al., "Essential role for natural killer cells in the lethal lipopolysaccharide-induced Shwartzman-like reaction in mice", Eur. J. Immunol. 24: 1155-1160, 1994.

Melendez-Vasquez, C. et al., "Immunological Investigation of Chronic Inflammatory Demyelinating Polyradiculoneuropathy", Journal of Neuroimmunology, vol. 73(3), 1997, 124-134.

Reinhart, K. et al., "Sepsis und septischer Schock", Intensivmedizin, Georg Thieme Verlag, Stuttgart (2001) 756-760.

Beishuizen, A. et al., "Endogenous Mediators in Sepsis and Septic Shock", Advances in Clinical Chemistry, vol. 33, 1998, 55-131.

Gabay, C. et al., "Acute-Phase Proteins and Other Systemic Responses to Inflammation", The New England Journal of Medicine, vol. 340(6), Feb. 11, 1999, 448-454.

Assicot, M. et al., "High Serum Procalcitonin Concentrations in Patients with Sepsis and Infection", The Lance, vol. 341, Feb. 27, 1993, 515-518.

Karzai, W., et al., "Procalcitonin—A New Indicator of the Systemic Response to Severe Infections", Infection, vol. 25 (6), Nov. 1997, 329-334.

http://www.medecine-worldwide.de/krankheiten/krebs/-xxx.html, wobei/ xxx zu ersetzen ist z.B. durch/allgemeines; / lungenkrebs; /brustkrebs; /prostatakrebs; /darmkrebs; /leukaemie; /corpuskarzinum, 2002.

Thomas, Lothar et al., (Herausgeber), Labor und Diagnose, 5. erw. Auflage, Kapital 34: Tumormarjer, S. 956-1019, 2000.

Pross, Hugh F. et al., "Role of Natural Killer Cells in Cancer", Nat Immun, 1993, vol. 12, pp. 279-292.

Lanier, Lewis L. et al., "Arousal and Inhibition of Human NK Cells", Immunological Reviews, 1997, vol. 155; pp. 145-154.

Fujii, Yoichi et al., "IgG Antobodies to Asialo $GM_1$ are More Sensitive than IgM Antobodies to Kill in vivo Natural Killer Cells and Prematured Cytotoxic T Lymphocytes of Mouse Spleen", Microbiol. Immunol., vol. 34, No. 6, 1990, pp. 533-542.

Volpe, Carmine M. et al., "$AsGM_1+$ NK Cells Prevent Metastasis of Invading LD-MCA-38 Tumor Cells in the Nude Mouse", Journal of Surgical Research, vol. 84, 1999, pp. 157-161.

Wilson, Susan D. et al., "Correlation of Suppressed Natural Killer Cell Activity with Altered Host Resistance Models in B6C3F1 Mice", Toxicology and Applied Pharmacology, vol. 177, 2001, pp. 208-218.

Yoshino, H. et al., "Natural Killer Cell Depletion by Anti-Asialo $GM_1$ Antiserum Treatment Enhances Human Hematopoietic Stem Cell Engraftment in NOD/Shi-scid Mice", Bone Marrow Transplantation, vol. 26, 2000, pp. 1211-1216.

Saijo, N. et al., "Analysis of Metastatic Spread and Growth of Tumor Cells in Mice with Depressed Natural Killer Activity by Anti-asialo $GM_1$ Antibody or Anticancer Agents", Journal of Cancer Research Clinical Oncology, vol. 107, 1984, pp. 157-163.

Habu, Sonoko et al., "Role of Natural Killer Cells Against Tumor Growth in Nude Mice—a Brief Review", Tokai J. Exp. Clin. Med., vol. 8, No. 5, 1983, pp. 465-468.

Lanier, Lewis L., "NK Cell Receptors", Annu, Rev. Immunol., vol. 16, 1998, pp. 359-393.

Whiteside, Teresa L. et al., "The Role of Natural Killer Cells in Immune Surveillance of Cancer", Current Opinion in Immunology, vol. 7, 1995, pp. 704-710.

Timonen, Tuomo et al., "Natural Killer Cell-Target Cell Interactions", Current Opinion in Cell Biology, vol. 9, 1997, pp. 667-673.

Rodriguez, Jose Abad et al., "Plasma Membrane Ganglioside Sialidase Regulates Axonal Growth and Regeneration in Hippocampal Neurons in Culture", Journal of Neuroscience, Nov. 1, 2001, vol. 21, No. 21, pp. 8387-8395.

Miles, Lindsay A. et al., "Gangliosides Interact Directly with Plasminogen and Urokinase and May Mediate Binding of These Fibrinolytic Components to Cells", Biochemistry, 1989, vol. 28, pp. 9337-9343.

Oshima, Haruyuki et al., "Gangliosides can Activate Human Alternative Complement Pathway", International Immunology, 1993, vol. 5, No. 10, pp. 1349-1351.

Nobile-Orazio, Eduardo, "Multifocal Motor Neuropathy", Journal of Neuroimmunology, 2001, vol. 115, pp. 4-18.

Quattrini, Angelo et al., "Human IgM Anti- $Gm_1$ Autoantibodies Modulate Intracellular Calcium Homeostasis in Neuroblastoma Cells", Journal of Neuroimmunology, 2001, vol. 114, pp. 213-219.

Uetz-von Allmen, Edith et al., "Antiganglioside GM1 Antibodies and Their Complement Activating Capacity in Central and Peripheral Nervous System Disorders and in Controls", Eur Neurol, 1998, vol. 39, pp. 103-110.

Hirota, Nobuyuki et al., "The Physiological Effect of Anti- $GM_1$ Antibodies on Saltatory Conduction and Transmembrane Currents in Single Motor Axons", Brain, 1997, vol. 120, pp. 2159-2169.

Ilyas, Amjad A. et al., "Anti- $GM_1$ IgA Antibodies in Guillain-Barré Syndrome", Journal of Neuroimmunology, 1992, vol. 36, pp. 69-76.

Kornberg, Andrew J., "Anti- $G_{M1}$ Ganglioside Antibodies: Their Role in the Diagnosis and Pathogenesis of Immune-Mediated Motor Neuropathies", Journal of Clinical Neuroscience, 2000, vol. 7, No. 3, pp. 191-194.

Bansal, A.S. et al., "IgM Ganglioside $GM_1$ Antibodies in Patients with Autoimmune Disease or Neuropathy, and Controls", Journal of Clinical Pathology, 1994, vol. 47, pp. 300-302.

Guijo, Carmen Garcia et al., "Presence and Isotype of Anti-Ganglioside Antibodies in Healthy Persons, Motor Neuron Disease, Peripheral Neuropathy, and Other Diseases of the Nervous System", Journal of Neuroimmunology, 1995, vol. 56, pp. 27-33.

Thomas, Florina P., "Antibodies to $GM_1$ and $Gal(\beta1-3)$ GaINAc at the Nodes of Ranvier in Human and Experimental Autoimmune Neuropathy", Microscopy Research and Technique, 1996, vol. 34, pp. 536-543.

Gatterbauer, B. et al., "Antiglycosphingolipid Immune Responses in Neurology", Annals New York Academy of Sciences, pp. 353-362, 1998.

Willison, H.J. et al., "Antiglycolipid Antibodies, Immunoglobulins and Paraproteins in Motor Neuron Disease: a Population Based Case-Control Study", Journal of Neurological Sciences, 1993, vol. 114, pp. 209-215.

Chowdry D. et al., "Axonal Guillain-Barré Syndrome: a Critical Review", Acta Neurol Scand, 2001, vol. 103, pp. 267-277.

Chapman, Joab et al., "Antibodies to Ganglioside $GM_1$ in Patients with Alzheimer's Disease", Neuroscience Letters, 1988, vol. 86, pp. 235-240.

Oczenski, W. et al., "Procalcitonin: a new parameter for the diagnosis of bacterial infection in the peri-operative period", European Journal of Anaesthiology, vol. 15, 1998, 202-209.

Redl, H. et al., "Procalcitonin Release Patterns in a Baboon Model of Trauma and Sepsis: Relationship to cytokines and neopterin", Crit Care Med., vol. 28(11), 2000, 3659-3663.

Redl, H. and G. Schlag, "Non-Human Primate Models of Sepsis", Sepsis, vol. 2, 1998, 243-253.

Panacek, E.A., "Anti-TNF strategies", Journal für Anästhesie und Intensivbehandlung, Feb. 2001, 4-5.

Calandra, T. et al., "Protection from septic shock by neutralization of macrophage migration inhibitory factor", Nature Medicine, vol. 6(2), Feb. 2000, 164-170.

The Merck Manuals Online Medical Library (online). Whitehouse Station, NJ: Merck Research Laboratories, 2006-2007. (retrieved on Nov. 19, 2007 from the Internet: <URL: http://www.merck.com/mmpe/print/sec06/ch068/ch068a.html>. Sepsis and Septic Shock. see pp. 1-5.

Sawada et al., "Anti-asialo GM1 antibody in sera from patients with Graves Disease adn Hashimoto's Thyroiditis", Lancet 2:8187, 1980.

Kielian et al., "CD14 and other recognition molecules for lipopolysaccharide: a review", Immunopharnn. 29: 187-205, 1995.

Wirguin et al., "Monoclonal IgM Antibodies to GM1 and Asialo-GM1 in Chronic Neuropathies Cross-React with *Campylobacter jejuni* Lipopolysaccharides", Ann. Neurol. 35:698-703, 1994.

Hirano et al., "Anti Asialo GM1 antibody detected in the patients' sera from systemic lupus erythematosus and Behcet's diseases with neurological manifestations", Jpn. J. Med. 27(2): 167-171, 1988.

Badgwell et al., "Natural Killer cells contribute to the lethality of a murine model of *Escerichi coli* infection", Surgery 132:205-212, 2002.

* cited by examiner

US 7,622,262 B2

METHOD FOR DIAGNOSING NEOPLASMS

CROSS REFERENCE TO RELATED APPLICATION

This application is the National Phase application of International Application No. PCT/EP03/03552, filed Apr. 4, 2003, which designated the United States and was published in English. The related International application, in its entirety, is incorporated herein by reference.

The invention relates to a method for diagnosing neoplasms in a human patient, in particular for the early diagnosis thereof, and for estimating the risk to a human patient due to the formation and/or spread of malignant neoplasms, by determining a "universal cancer marker substance" in a biological sample.

The marker substance determined according to the invention is a humoral marker substance which indicates with very high sensitivity (correct detection of samples of persons suffering from the disease) the presence of neoplasms in patients and additionally a particular risk situation/prognosis for patients in whom such neoplasms are not yet clinically manifest but who, because of, for example, their circumstances of life (for example exposure during work; smoking) and/or a previous disease and/or medical treatment, are exposed to a particular statistical risk of developing a malignant neoplastic disease.

In the context of the present Application, the term "neoplasm" is used as a general term or synonym for tumours, in particular malignant tumours, as are typical for cancer diseases (carcinomas). In a country such as Germany, more than 300,000 men and women contract malignant neoplasms, i.e. cancer, every year, the number of new cancer cases diagnosed annually and the mortality being considerable (cf. (1); in the description below, cross-references to sources are generally given as numbers in brackets; the numbers relate to the list of references at the end of the description). Malignant neoplasms can form in virtually any tissue or organ and, depending on the organ affected, a distinction is made between numerous cancer diseases which may differ considerably from one another with respect to their statistical frequency, prognosis and treatability.

Recent years have seen the development of a large number of therapies which have resulted in considerable progress in the curability of numerous forms of cancer diseases. In all cases, however, the prospects of curing cancer diseases are always better the earlier the cancer disease is diagnosed. Early diagnosis of cancer, i.e. diagnosis of neoplasms, at a time when there are as yet no or no significant clinical symptoms, is very particularly important.

For the detection of neoplasms as early as possible in clinical diagnosis, so-called "tumour markers" are determined in biological samples, in particular blood samples and body secretions, of patients investigated. Tumour markers are substances which are either formed directly by malignant tumour cells or which form because tumour cells induce the synthesis of the respective marker in non-tumour cells. If tumour markers are localized in increased concentration in biological fluid samples (humoral tumour markers) or in tissue (cellular tumour markers), they permit conclusions about the presence, the course and the prognosis of a tumour disease. The tumour markers currently introduced in clinical diagnostic practice may be oncofoetal antigens, carbohydrate epitopes detectable with monoclonal antibodies, enzymes, isoenzymes, oncogenic products and receptors. An overview of the tumour markers currently used in clinical diagnosis is to be found in (2).

Common to all currently determined tumour markers is the fact that, on the one hand, they have a relatively high organ specificity but that the sensitivity of their determination is at the same time relatively limited. The relatively high organ specificity of the tumour markers currently determined has on the one hand the advantage that their detection simultaneously provides information about the organ in which the causal cancer disease has occurred with high probability. However, the high specificity is a disadvantage in that cancer diseases of other organs are not diagnosable in the determination of organ-specific tumour markers, or the simultaneous determination of numerous different tumour markers is required for a comprehensive early diagnosis of cancer. The relatively low sensitivity of the determination of the known tumour markers (with a high sensitivity of a determination, most or all patients are correctly diagnosed), which is between 20 and 80%, depending on cancer disease and tumour marker, results in the risk of nondiagnosis of cancer diseases still being very high in spite of the determination of the tumour markers suitable per se for the purpose.

In view of the situation described, it would be extremely desirable to have a method which provides reliable information about the presence of any tumour disease (i.e. malignant neoplasms) with a very high sensitivity, so that, optionally by additionally taking into account the clinical picture of the patient investigated in order to avoid misinterpretations of the measured results, optionally further diagnostic measures for more exact localization and differential diagnosis of the neoplastic disease detected are then justified. At the same time, healthy persons should usually be capable of being diagnosed as such in such a method, so that a diagnostic false alarm can as far as possible be avoided. There is at present still no method which meets the requirement described and, in view of the high specificity and sensitivity differences of the tumour markers known to date, there is also little cause for hope that a universal, highly sensitive tumour marker having a low organ specificity would exist at all and would be capable of being made utilizable for clinical diagnosis.

The present invention is based on the extremely surprising finding that a certain antibody or autoantibody known per se in other contexts, provided it can currently be experimentally checked, is found at diagnostically significantly increased levels in all tested malignant neoplasms (cancer types) in biological samples, in particular patient sera, while the same antibody is not detectable in healthy normal persons or is detectable only in substantially smaller amounts. By determining this antibody, it is possible, according to the present invention, to detect with high reliability the presence of malignant neoplasms in patients or persons who undergo a routine examination or participate in a series investigation, without a significant number of healthy normal persons being determined as false positive. If the antibody determined also occurs in increased concentrations in some other special diseases, a correct interpretation of the results of measurements is as a rule possible without major difficulties on the basis of additional clinical findings.

According to the present invention, a method is therefore provided which can be designated as a method for the diagnosis, in particular for the early diagnosis, of neoplasms in a patient and for the estimation of its risk due to the formation and/or spread of malignant neoplasms, in which the presence and amount of antibodies which bind to ganglioside structures and to antigen structures simulating ganglioside structures, especially of antibodies binding to monosialo-$G_{M1}$ (anti-$G_{M1}$ antibodies) and/or antibodies binding to asialo-$G_{M1}$ antibodies (anti-$AG_{M1}$ antibodies) of the IgG and/or IgA type, are determined in a biological sample of the patient, and the presence of such antibodies and/or their amount significantly increased compared with normal persons are correlated with the presence of a neoplasm and/or an increased risk to the patient due to malignant neoplasms.

A particularly important aspect of the present invention can be summarized as the use of antibodies of the IgG and/or IgA type which bind to $AG_{M1}$ as universal markers for the early diagnosis and prognosis of malignant neoplastic diseases and for the estimation of the risk to a patient that he will develop a malignant neoplastic disease.

The discovery of the diagnostic method according to the invention, with a presentation of the measured values on which this method is based, and a currently preferred procedure for carrying it out in practice are explained in more detail below. An interpretation and ex-post plausibilization of the method according to the invention in the light of scientific publications which can be related to the subject matter of the present invention are given below and show that the determination, according to the invention, of anti-ganglioside antibodies or autoantibodies, in particular of those of said type, is also of considerable importance for a novel interpretation of the origin or development of cancer, the findings on which the present invention is based providing clear indications of novel therapeutic approaches to cancer prevention, cancer inhibition and optionally cancer treatment.

The present invention is a result of intensive research by the Applicant in the area of the clinical diagnosis of autoimmune diseases. It starts from the knowledge that the antibodies which are discussed in the literature in conjunction with autoimmune diseases, in particular nerve-damaging, neuropathic autoimmune diseases, also include certain anti-ganglioside antibodies.

Gangliosides are glycolipids which are constituents of the extracellular side of the plasma membrane of animal cells and as such also occur in nerve tissue. They contain several monosaccharide units per mole but have no phosphorus content and are assigned to the sphingolipids. Compared with proteins, they tend to be low molecular weight biomolecules. The gangliosides to which the antibodies discussed in the context of the present invention bind are the monosialo-ganglioside referred to generally as $G_{M1}$ and the associated "asialo" compound $AG_{M1}$. $G_{M1}$ has a polysaccharide chain of 4 sugar monomer units which comprise two D-galactose units, one N-acetylgalactosamine unit and one D-glucose unit, the latter being bound to a ceramide moiety. In the ganglioside $G_{M1}$, an N-acetylneuraminic acid radical (NANA; sialic acid or o-sialinic acid radical; "monosialo" radical), which is missing in the sialinic acid-free asialo-$G_{M1}$ ($AG_{M1}$), is bound to the D-galactose unit arranged inside the polysaccharide chain.

Said gangliosides and related compounds are associated with numerous important biological functions of the human body, including, for example, axonal growth and neuronal differentiation, receptor functions and participations in various immune reactions of the body and in signal transduction and cell-cell recognition. In this context, reference is made, for example, to (14 to 26).

It has long been known that antibodies or autoantibodies which bind to said and related gangliosides can occur in the human body. The physiological role thereof and their possible importance for clinical diagnosis form the subject of numerous scientific investigations.

By far the predominant part of all published papers are concerned with the role and the diagnostic significance of anti-ganglioside antibodies in neuropathies, for example in immunomediated motor neuropathies, such as Guillain-Barré syndrome (radiculoneuritis, polyradiculitis) and the related (Miller-)Fisher syndrome (cf. e.g. 27 to 43; 63). An increased occurrence of anti-$G_{M1}$ autoantibodies in some patients was also reported in association with Alzheimer's disease (42). Furthermore, they were found in individual HIV patients (55 to 57). Individual experiments for their determination in association with certain cancer types were also reported (58 to 60), but only few informative results or results with a low sensitivity were obtained, which will be discussed in more detail below.

If the relevant publications are studied more carefully, what is striking is that, despite the similarity of the observations, the findings and information relating to the amounts to be observed—which as a rule tend to be small—and types of the various (auto)antibodies in the various patients differ relatively greatly from one another in detail. This is sufficient to lead to the conclusion that the determination of such antibodies is only of limited to doubtful value for clinical diagnosis (39, 62).

On the basis of the literature data, which in some cases diverge considerably, the Applicant gained the impression that one reason for this might lie in the methodology, and, owing to systematic errors of the measuring methods used, no truly reliable, informative results are available to date. Most of the determinations for which results were published were carried out by means of immunoassays of the ELISA type, which were designed to employ a solid phase to which gangliosides—partly obtained by the authors themselves from biological material—were bound. This solid phase was reacted with the biological fluid sample in which the antibodies to be determined were presumed to be present. After the respective chosen incubation time, a solid-liquid separation and washing of the solid phase, human antibodies bound to said solid phase were then marked unspecifically with enzyme-marked animal anti-human Ig antibodies and were determined.

When applied to the anti-ganglioside antibody determination, such an assay scheme is extremely susceptible to disturbances and errors of measurement and is capable of giving reliable, reproducible results only on careful standardization and normalization. One of the reasons for this is that the quality of the solid phase which is obtained by immobilizing the relatively low molecular weight gangliosides is liable to considerable variations. This is partly due to the fact that, before the reaction with the fluid sample, remaining free binding capacities of the solid phase have to be saturated. As a rule, bovine serum albumin, i.e. a protein, is used for this purpose. However, this step results in the unspecific binding of other proteins, for example those of the IgG type, from the sample being very high, which leads to a strong background signal, against which the antibodies to be determined have to be determined. If, however, the sensitivity of an assay is not very high—which is as a rule the case with assays of the ELISA type—background signals and measured signals can be superposed to such an extent that incorrect (false negative or false positive) or unreliably reproducible measured results are obtained. Regarding the various assay methods used and the systematic and practical problems in the application of such methods to the determination of anti-ganglioside antibodies, reference may be made, for example, to (64 to 68), in particular (66) being concerned intensively with the problem of the practical determination of anti-ganglioside antibodies.

In view of this initial situation, the Applicant had decided to tackle the problem of the reproducible determination of anti-$G_{M1}$ and anti-$AG_{M1}$ antibodies and the diagnostic significance of such a determination, for example in Alzheimer's patients, and to make use of the particular experience and means available to the Applicant as a producer of assays for the clinical diagnosis of autoantibodies. For internal research, the Applicant developed variants of an improved modification of the previously known anti-ganglioside assays, while maintaining all customary quality standards. The measurements carried out using these improved assays on antibodies binding to $G_{M1}$ or $AG_{M1}$ in sera of a reference group of normal persons (blood donors) without clinically relevant pathological findings and in sera of various patients surprisingly showed, as will be described further below, that highly significantly increased titres for anti-$G_{M1}$ or anti-$AG_{M1}$ antibodies of the IgA and of the IgG type, but not of the IgM type, were found in all sera available to the Applicant and obtained from patients suffering from cancer, in comparison with normal persons, in particular with a sensitivity which reached virtually 100%, and that these significantly increased titres were found in all cancer sera without a selectivity with respect to some particular cancer disease being detectable. This finding was extremely surprising and is in contrast to all experience to date with biomolecules investigated or used as tumour markers.

Although the results described in more detail below were obtained using a certain improved ligand binding assay ("immunoassay") from the Applicant's laboratory, the use of the knowledge obtained is possible not only with an assay of the special format described. Rather, it is assumed that the specific assay described below is still substantially suboptimal for the antibody assay in question, and that commercial assays for the clinical determination of anti-ganglioside antibodies, in particular of anti-$G_{M1}$ and anti-$AG_{M1}$ (auto)antibodies, will, after optimization, differ substantially in many respects from the assay described.

The methods for the determination of said antibodies in a biological sample may be any known immunodiagnostic methods which are used for detecting and for measuring antibodies (autoantibodies). Preferably, the antibodies are determined with the aid of a ligand binding assay, in which the respective ganglioside in immobilized form is used as an antigen for binding the antibodies sought. For marking the antibodies specifically bound from a biological sample, it is then possible to use anti-human antibodies marked in any suitable manner known per se, marked gangliosides or binders simulating the carbohydrate structure thereof and having an affinity suitable for the respective assay format.

Competitive assay formats may also have particular advantages. Preferably, instead of enzyme marking, another marking is chosen, for example marking for a chemiluminescence detection reaction, e.g. an acridinium ester. It is of course preferable to use, for the antibody determination, an assay which ensures the required high sensitivity in the range of the antibody concentrations occurring and permits separation of the measured signals from the assay background.

The assay method can be adapted to chip technology or designed as an accelerated test (point-of-care test).

In order to avoid unjustifiably narrow and restrictive interpretations of the terms used in the present Application and the associated claims, some of the most important terms are to be defined in particular below for the purposes of the present Application:

"Antibody": This term includes, without distinguishing between different methods of genesis and formation, antibodies both against external antigens and against endogenous structures, i.e. autoantibodies, where the latter may also have become autoantibodies by antigen cross-reactions from antibodies against external antigens and may have preserved their binding capability with respect to external antigens.

When, for example, it is stated that an antibody binds "to ganglioside structures and to antigen structures simulating ganglioside structures" or is "reactive towards gangliosides or certain gangliosides", where reactive means "reactive in the context of specific binding", it should be sufficiently defined by this definition without, for example, its specific binding also to additional other antigen structures, or its practical determination using reagents (for immobilization or marking or as competitors) with molecular structures which only simulate $AG_{M1}$, in particular the carbohydrate structure thereof, playing a role for the definition as antibodies according to the invention.

"Ganglioside" In the context of the present invention, the term "ganglioside" primarily represents the gangliosides $AG_{M1}$ in the characterization of the binding behaviour of the antibodies to be determined. However, the term is also intended to include related gangliosides not investigated to date, e.g. fucosylated gangliosides if it is found that antibodies also binding to these gangliosides and having a comparable diagnostic significance for neoplasms are found in cancer sera.

"Assay" This term covers any highly sensitive ligand binding assays suitable for a determination of the (auto)antibodies in question, without any restriction to a certain assay format (sandwich assay, competitive assay, agglutination assay) or a certain type of marking being desired. Of course, certain assay formats and/or markings are superior to others and are therefore preferred (for example, chemiluminescence marking over enzyme marking). However, the use of an assay which is poorer or better than the assay described specifically below is not intended to depart from the scope of the claims if it serves the diagnostic purposes defined in the present Application.

"Sensitivity" In the context of the present invention, a high sensitivity means that the antibodies are found in at least 50%, better 70%, preferably at least 50% and even more preferably at least' 95% of all patients suffering from cancer.

"Universal" This term, like the term "unspecific", in conjunction with terms such as "biomarker" or "cancer or tumour marker", means that there is no specificity for a certain cancer disease and the marker is found in diagnostically significant amounts in substantially all cancer diseases, at least in all customary cancer diseases of the internal organs and metastatic cancer diseases, and very particularly in the cancer diseases mentioned below under the numbers 1 to 13 in table 5.

Further meanings of the terms are evident to a person skilled in the art from the introductory and following description of the invention and its embodiments.

In the description below, in addition to the content of some tables, reference is also made to figures, which show the following:

Figure 1:
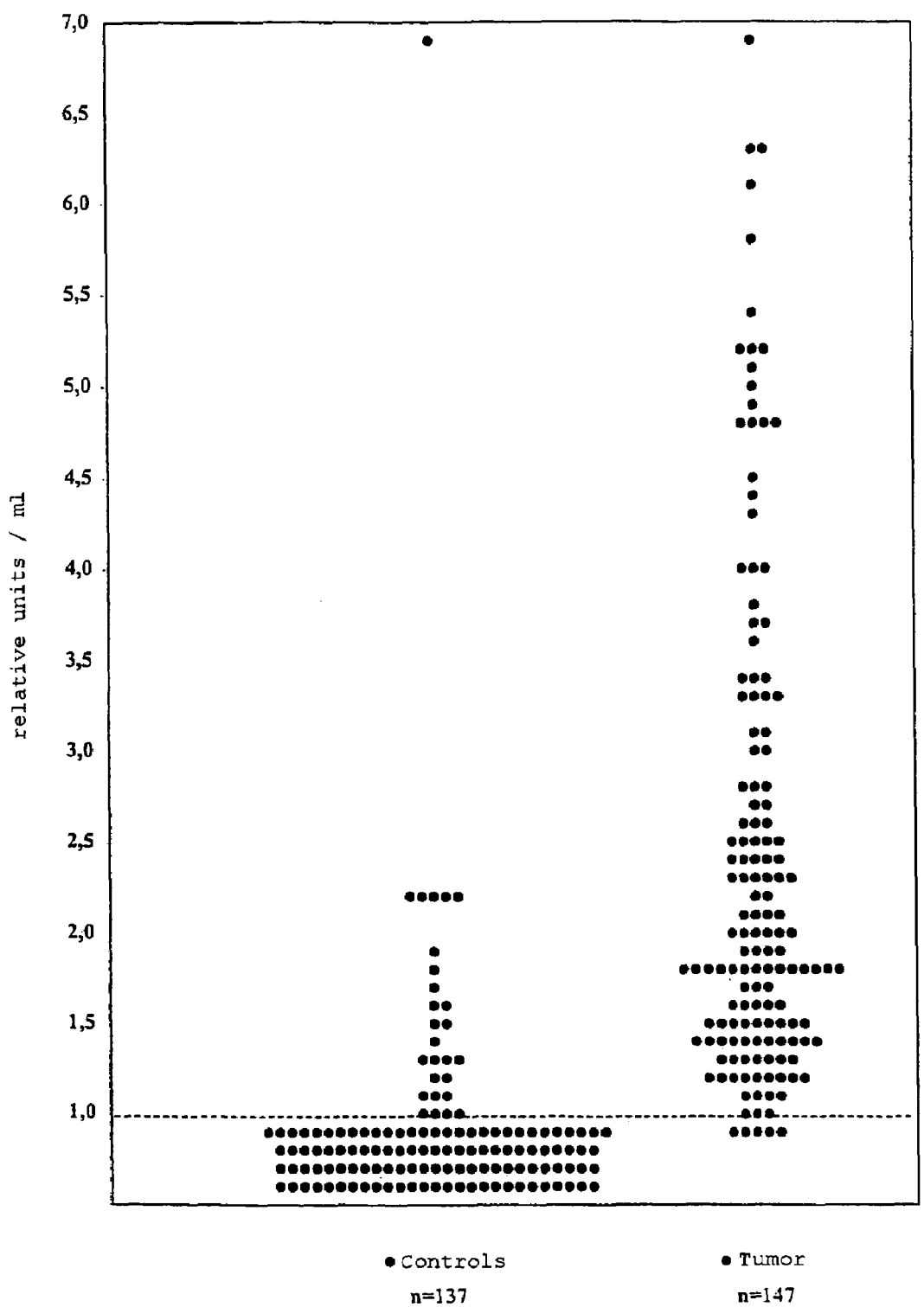
FIG. 1 shows a graph of the results of the measurement of antibodies of the IgG class which bind to monosialo-$G_{M1}$, in sera of 137 control persons, compared with the results of the measurement of sera of 147 tumour patients.
Figure 2:
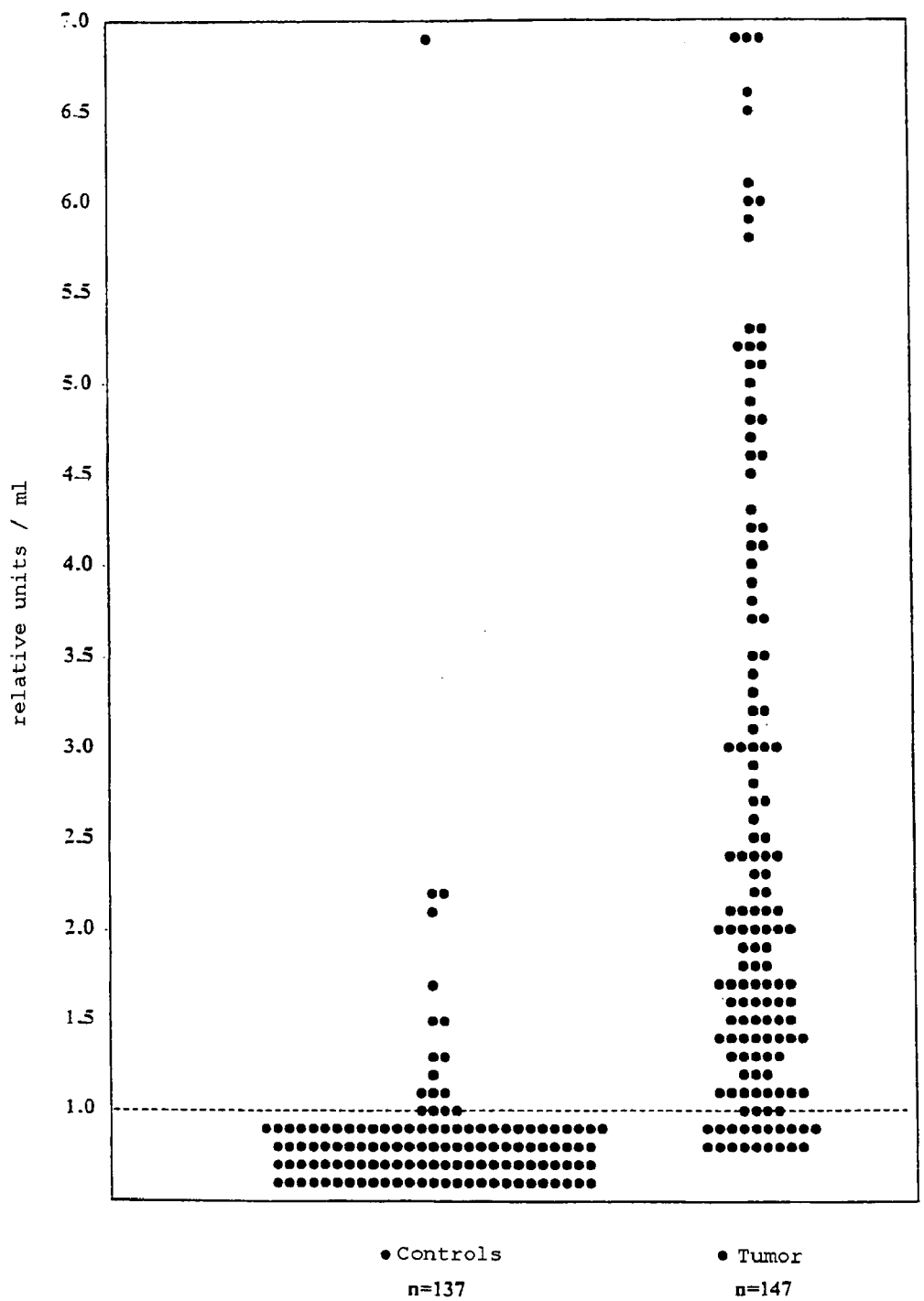
FIG. 2 shows the results of a measurement of the same sera as in FIG. 1 for antibodies of the IgA class which bind to monosialo-$G_{M1}$.
Figure 3:
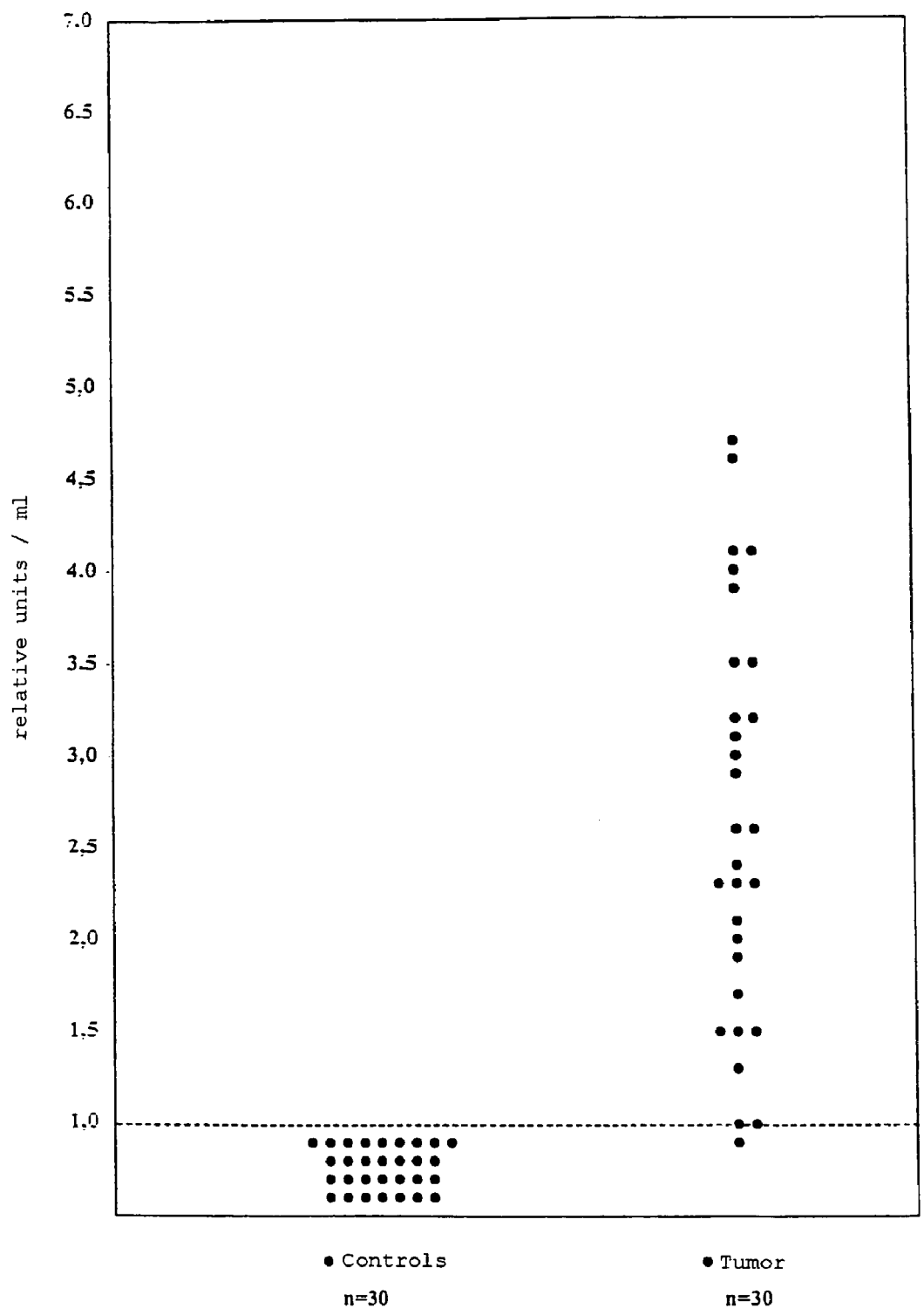
FIG. 3 shows the results of the determination of antibodies of the IgG class which bind to asialo-$G_{M1}$, in sera of 30 normal persons (controls), compared with the results of the measurement of 30 tumour sera (all sera are partial groups of the sera measured in FIGS. 1 and 2)
Figure 4:
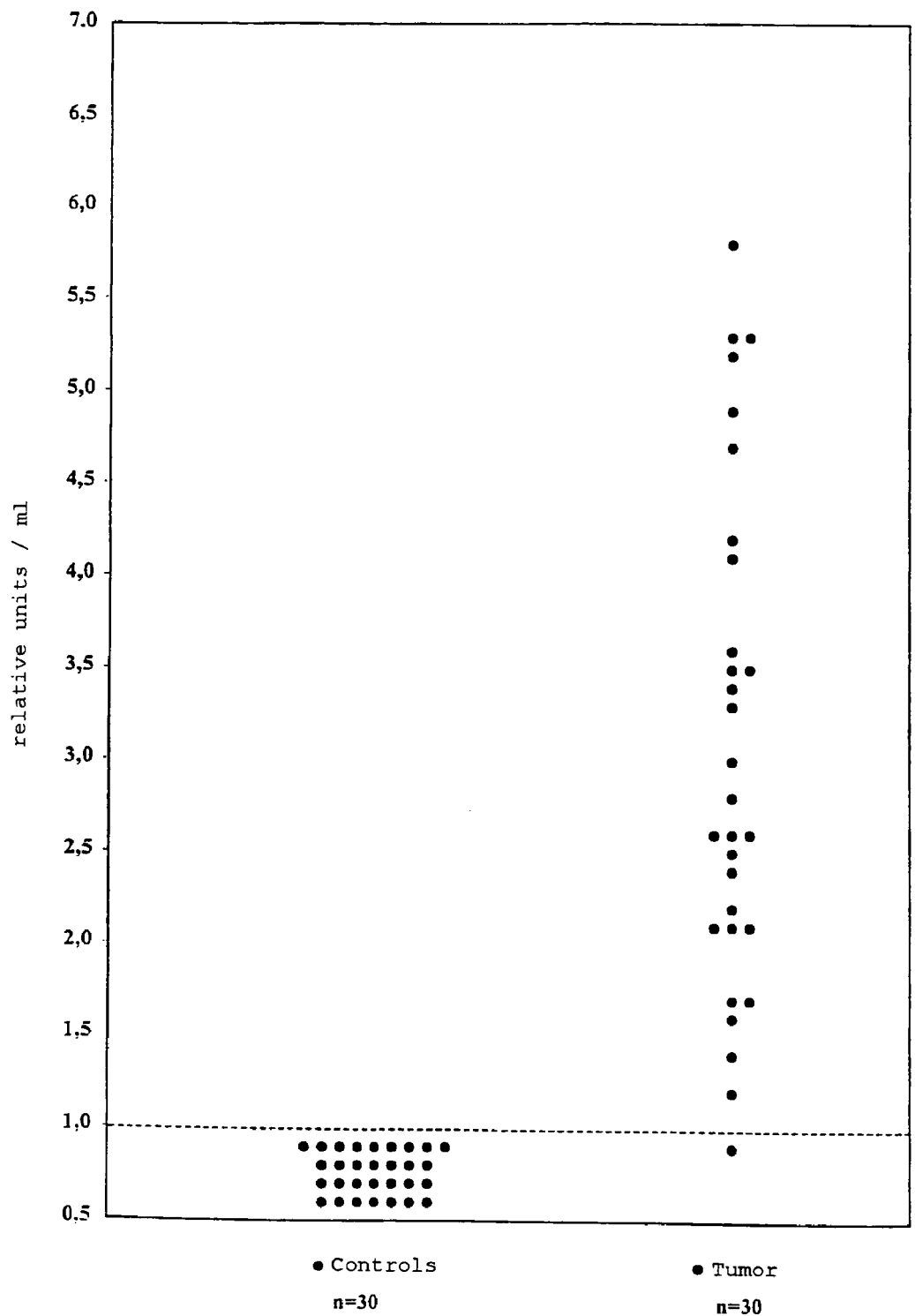
FIG. 4 shows the results of the determination of antibodies of the IgA class which bind to asialo-$G_{M1}$, in the same sera as in FIG. 3.
Figure 9:
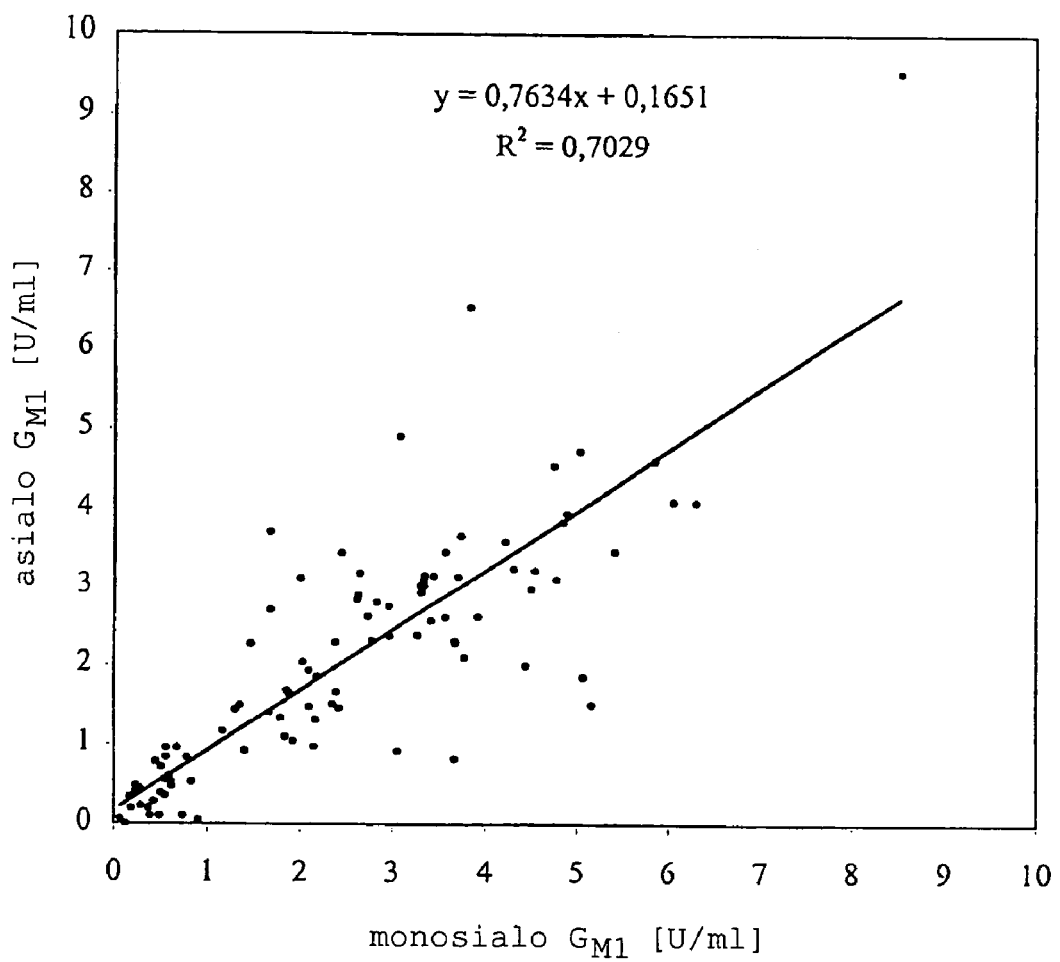
Figure 10:
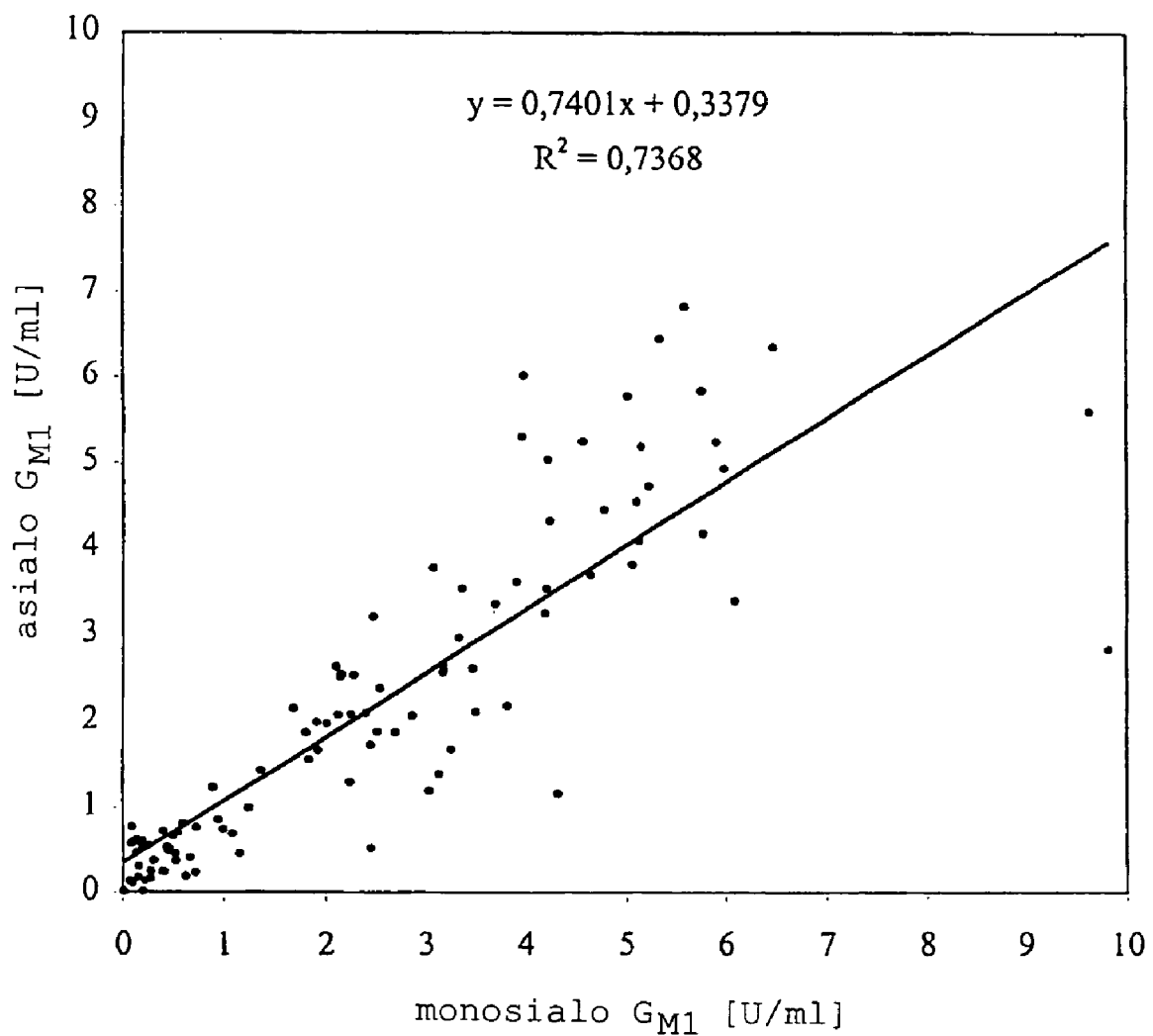

FIG. 9 shows a graph which correlates the results of the determinations, in the same partial group of sera, of antibodies of the IgG type which bind to monosialo-$G_{M1}$, and of the determination of antibodies of the IgG type which bind to asialo-$G_{M1}$ (cf. FIG. 1 and FIG. 3); and FIG. 10 shows a correlation, corresponding to FIG. 9, of the determination of antibodies of the IgA class according to FIG. 2 and FIG. 4.

Antibody Assays

1. Preparation of the Assay Components:

A. Preparation of Test Tubes (Coated Tubes; CT)

Three types of test tubes were prepared: (a) test tubes to which the gangliosides $G_{M1}$ and $AG_{M1}$ were bound, and (b) test tubes having a BSA coating for the determination of the background signal specific to the sample.

a) For the preparation of the ganglioside-coated test tubes (GA-CTs), the gangliosides ($G_{M1}$ and $AG_{M1}$, in each case obtained from Sigma, Germany) were dissolved in methanol and then diluted in PBS (phosphate-buffered saline solution), pH 7.2, 25% methanol, to a concentration of 5 µg/ml. In each case 300 µl of this solution were introduced into polystyrene tubes ("Star" polystyrene tubes from Greiner, Germany) and incubated at room temperature for 16 h. Thereafter, the content of the tubes was removed by suction, and the tubes were filled with 4.5 ml of 0.5% BSA (bovine serum albumin, protease-free, from Sigma, Germany) in water for saturating free binding sites and were incubated for 2 h at room temperature. Thereafter, the tube content was decanted and the tubes were filled with 0.2% Tween, 10 mM Tris/HCl, 10 mM NaCl, pH 7.5, and decanted again. The tubes were then used for the antibody assay.

b) Since serum constituents bind to the BSA used for saturating free binding sites of the test tube wall, and the degree of such binding may be very different in the case of different sera, it is necessary to determine, for each serum separately, the background signal specific to the sample.

For this purpose, the same test tubes were filled with 4.5 ml of 0.5% BSA in water and incubated for 2 h at room temperature. Thereafter, the tube content was decanted and the tubes were filled with 0.2% Tween, 10 mM Tris/HCl, 10 mM NaCl, pH 7.5, and decanted again. The tubes (HR-CTs) were then used for the determination of the background signal specific to the sample.

B. Preparation of Acridinium Ester-Marked Anti-Human IgG or Anti-Human IgA Antibodies (Tracers)

Goat anti-human IgG antibodies (affinity-purified; grade II, from Scantibodies, USA) or goat anti-human IgA antibodies (affinity-purified; from Sigma, Germany), in each case 2 mg/ml in PBS, pH 7.4, 100 µl, were each mixed with 10 µl of acridinium NHS ester (from Hoechst, Germany; 1 mg/ml in acetonitrile; cf. DE 36 28 573 A1) and incubated for 20 min at room temperature. After addition of 300 µl of 20 mM glycerol, 50 mM NaCl, the marked antibodies were purified by means of adsorption chromatography via hydroxyapatite HPLC. The separation column used was an HPHT column (120 mm×8 mm), equilibrated in solvent A (1 mM $NaPO_4$, pH 7.0, 10% methanol, 0.1% Lubrol; "LM A"; Lubrol 17A17 was obtained from Serva, Germany). The flow rate was 0.8 ml/min. Bound antibodies were eluted by means of a linear 40 min gradient from LM A/LM B (500 mM $NaPO_4$, pH 7.0, 10% methanol, 0.1% Lubrol; "LM B") at a flow rate of 0.8 ml/min. The column outflow was measured continuously by UV absorption at 280 nm (protein) and 368 nm (acridinium ester). Acridinium ester not bonded to protein was eluted in unbound form from the column and thus completely separated from the marked antibodies. The antibodies were eluted at about 25 min. After determination of the protein concentration (BCA method) of the HPLC-purified marked antibodies, the tracers were diluted to a final concentration of 0.1 µg/ml in PBS, pH 7.2, 1 mg/ml of goat IgG (from Sigma, Germany) and 1% BSA.

2. Carrying Out the Determination of Anti-Ganglioside Antibodies

The samples (human sera) to be investigated were diluted 1:20 with PBS, pH 7.2, 1 mg/ml of goat IgG, 1% BSA. In each case 10 µl thereof were pipetted into GA-CTs or HR-CTs. A 16 h incubation with shaking (IKA shaker KS250 basic, 400 rpm) was then effected at 4° C.

Unbound antibodies were removed by filling/decanting the tubes 5 times with 1 ml of 0.2% Tween, 10 mM Tris/HCl, 10 mM NaCl, pH 7.5. Antibodies which remained on the tube surfaces were detected by binding of marked goat anti-human IgG or marked goat anti-human IgA, by incubating the tubes with, in each case, 200 µl of the respective tracer (cf. above, 1.B.) and then for 3 h at 4° C. with shaking. Unbound tracer was removed by washing 5 times (as above).

The amount of the marked antibody which remained on the tube surface was measured by means of a luminescence measurement in a Berthold LB.952T/16 luminometer.

The luminescence signal of each sample, obtained for GA-CTs, was corrected by the respective background signal for the same sample, measured using the HR-CTs. The resulting signal (difference signal) is the signal for antibodies from the respective sample which bind to the gangliosides $G_{M1}$ and $AG_{M1}$. Dilution series of samples having a high content of anti-ganglioside antibodies were used as relative calibrators for the quantification.

3. Measurement of Sera of Healthy Normal Persons (Controls) and Cancer Patients

Using the test tubes prepared as described and using the method described above, the following series measurements were carried out: Control sera: 137 control sera (blood donor sera and, for avoiding age-related influences on the antibody concentrations, sera of normal persons of various ages from old people's homes and of the Applicant's employees) served as control sera for the antibody determinations using GA-CTs which were coated with $G_{M1}$. For the antibody determinations using GA-CTs which were coated with $AG_{M1}$, a partial group of these sera, which comprised only 30 sera, was measured.

Test sera: 147 sera of patients with clinically diagnosed tumours of various organs/tissues and, additionally, 20 sera of patients with chronic inflammatory intestinal diseases served as test sera for the antibody determinations using GA-CTs which were coated with $G_{M1}$. For each test serum there existed exact clinical documentation which permitted a classification of the sera of cancer patients, used in the measurement, according to the tumour type found in them. For the antibody determinations using GA-CTs which were coated with AGml, a partial group of these sera, which comprised only 30 sera of cancer patients, was measured.

The results of the determinations of antibodies of the IgG and IgA classes using GA-CTs which were coated with $G_{M1}$ are shown in FIGS. 1 and 2.

The results of the determinations of antibodies of the IgG and IgA classes using GA-CTs which were coated with $AG_{M1}$ are shown in FIGS. 3 and 4.

Figure 5:
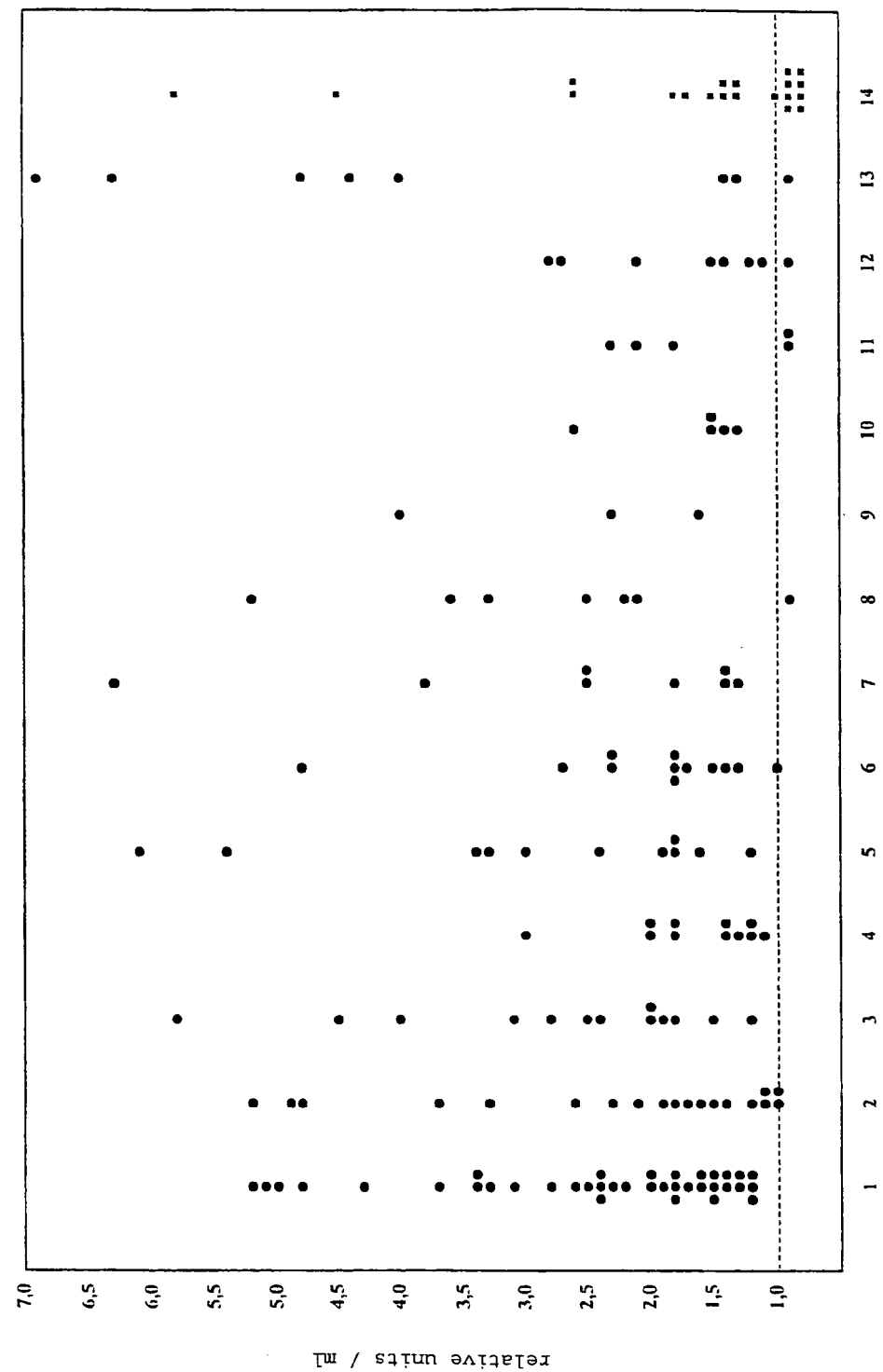
FIG. 5 shows a graph which classifies the antibody determination in the tumour sera according to FIG. 1 with respect to the clinically diagnosed tumour types/diseases, which are characterized by numbers from 1 to 14, the meaning of the numbers 1 to 14 being explained in the description below.

FIG. 5 shows a classification of the measured results according to FIG. 1 (IgG) according to clinical pictures. The index numbers plotted in the horizontal direction represent the clinical diagnoses shown in the list below:

| Index number | Diagnosis | Number of sera |
|---|---|---|
| 1 | Carcinoma of the colon | n = 37 |
| 2 | Carcinoma of the breast | m = 19 |
| 3 | Ovarian carcinoma | n = 13 |
| 4 | Carcinoma of the stomach | n = 11 |
| 5 | Carcinoma of the pancreas | n = 11 |
| 6 | Carcinoma of the oesophagus | n = 12 |
| 7 | Carcinoma of the gall bladder | n = 8 |
| 8 | Carcinoma of the liver | n = 7 |
| 9 | C cell carcinoma | n = 3 |
| 10 | Carcinoma of the thyroid | n = 5 |
| 11 | Carcinoma of the prostate | n = 5 |
| 12 | Carcinoma of the lung | n = 8 |
| 13 | Other carcinomas | n = 8 |
| 14 | Crohn's disease/ulcerative colitis | n = 20 |

The "other carcinomas" were distributed as follows:

Carcinoma of the appendix (n=1), carcinoma of the bladder (n=1), cardia carcinoma (n=1), distal verophagus carcinoma (n=2), carcinoma of the floor of the mouth (n=1), carcinoma of the kidney (n=1), epigastric tumour (n=1).

Figure 6:
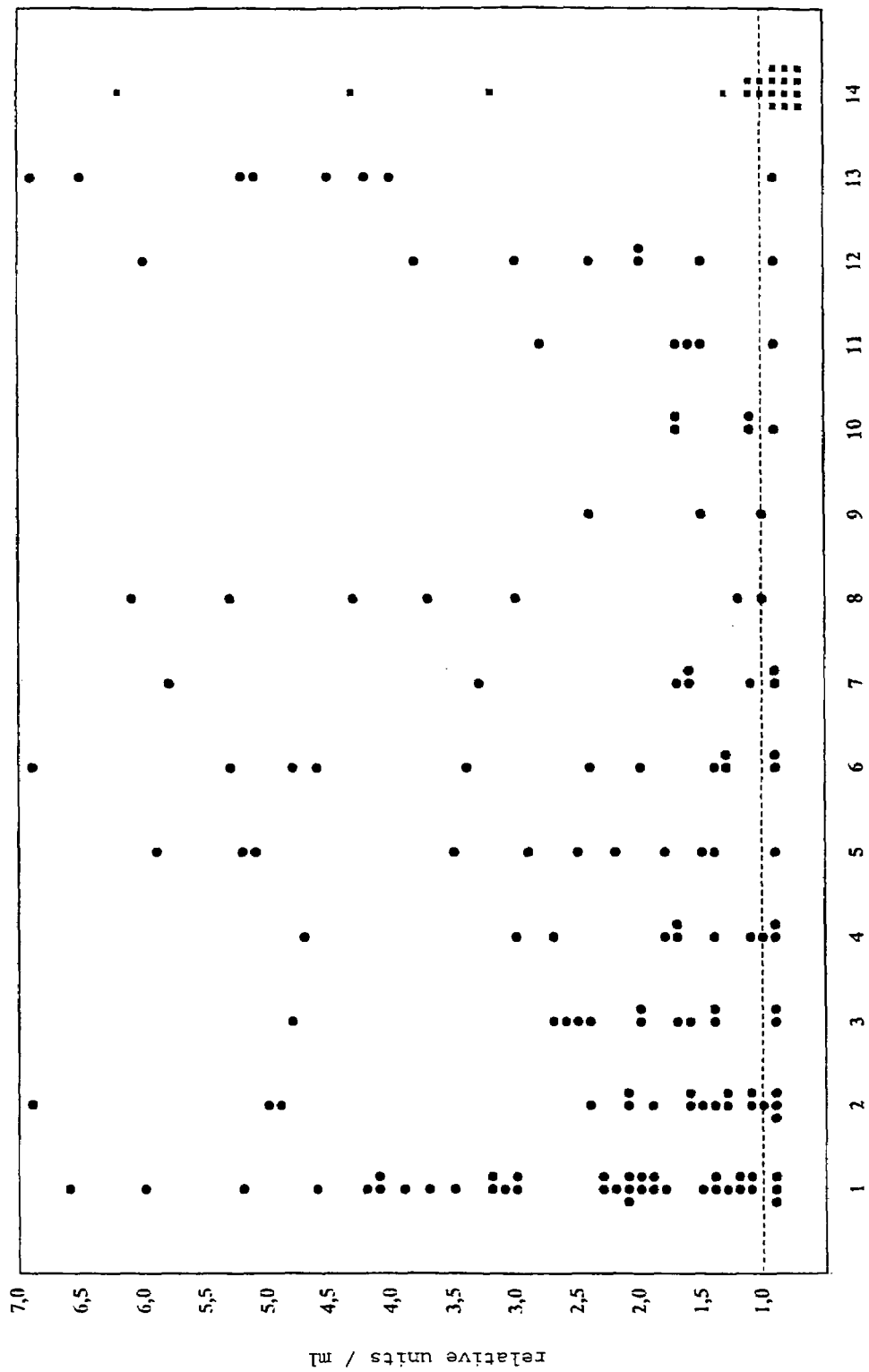
FIG. 6 shows a classification of the measurement of antibodies of the IgA class according to FIG. 2, corresponding to the classification of FIG. 5.

FIG. 6 shows a corresponding classification of the results from FIG. 2 (IgA).

Table 1 below summarizes the results of FIGS. 5 and 6 numerically.

TABLE 1

| Organ affected | anti-$GM_1$ IgG | anti-$G_{M1}$ IgA | n |
|---|---|---|---|
| Colon/Rectum | 38 = 100% | 35 = 92% | 38 |
| Breast | 19 = 100% | 16 = 84% | 19 |
| Ovaries | 13 = 100% | 11 = 85% | 13 |
| Stomach | 11 = 100% | 9 = 82% | 11 |
| Pancreas | 11 = 100% | 10 = 91% | 11 |
| Oesophagus | 12 = 100% | 10 = 83% | 12 |
| Gall bladder | 8 = 100% | 6 = 75% | 8 |
| Liver | 6 = 86% | 7 = 100% | 7 |
| C cell | 3 = 100% | 3 = 100% | 3 |
| Lung/Bronchia | 7 = 88% | 7 = 88% | 8 |
| Thyroid | 5 = 100% | 4 = 80% | 5 |
| Prostate | 3 = 60% | 4 = 80% | 5 |
| Other | 7 = 88% | 7 = 88% | 8 |

Figure 7:
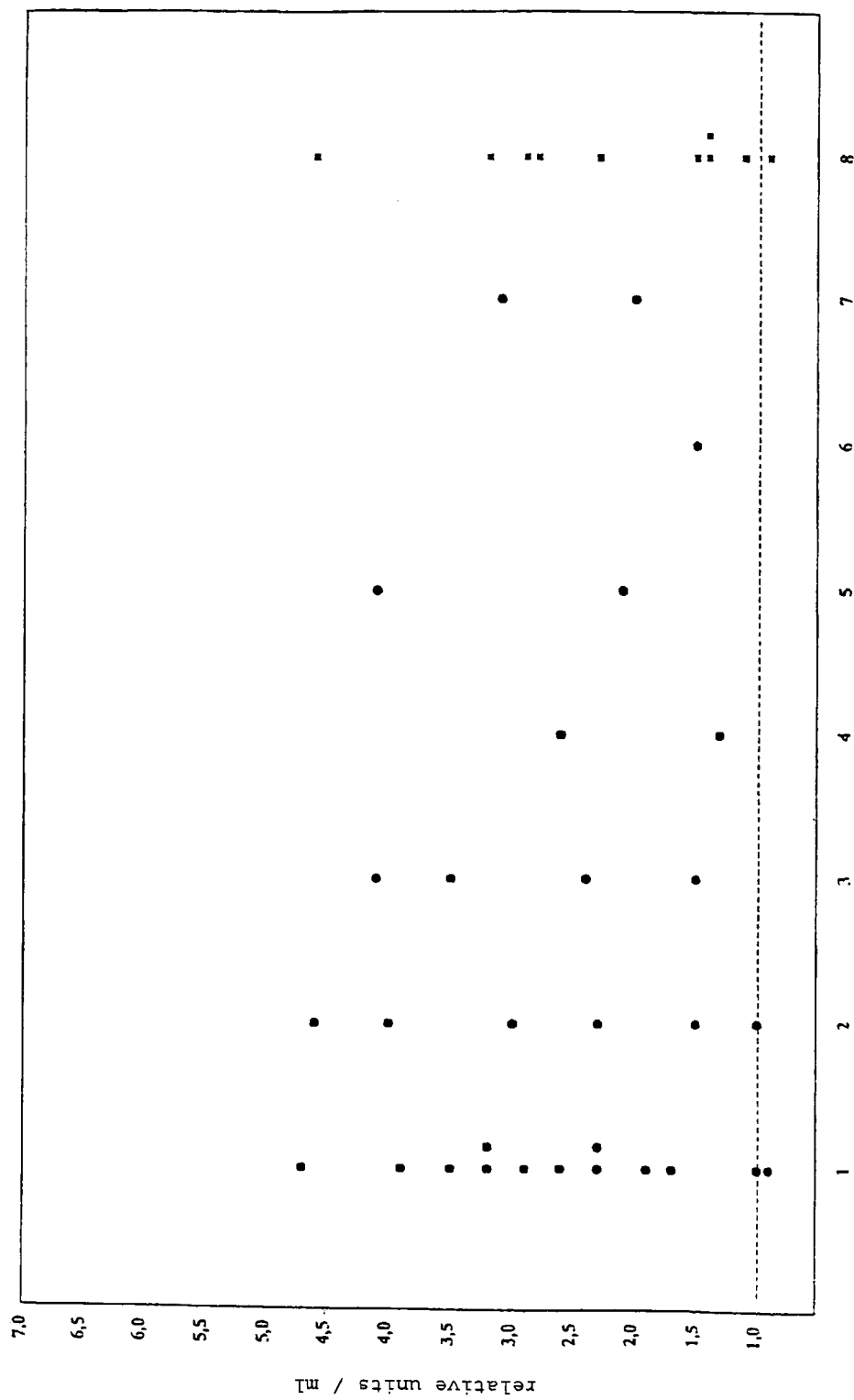
FIG. 7 shows a classification of the measurement of antibodies of the IgA class according to FIG. 3, corresponding to the classification of FIG. 5.
Figure 8:
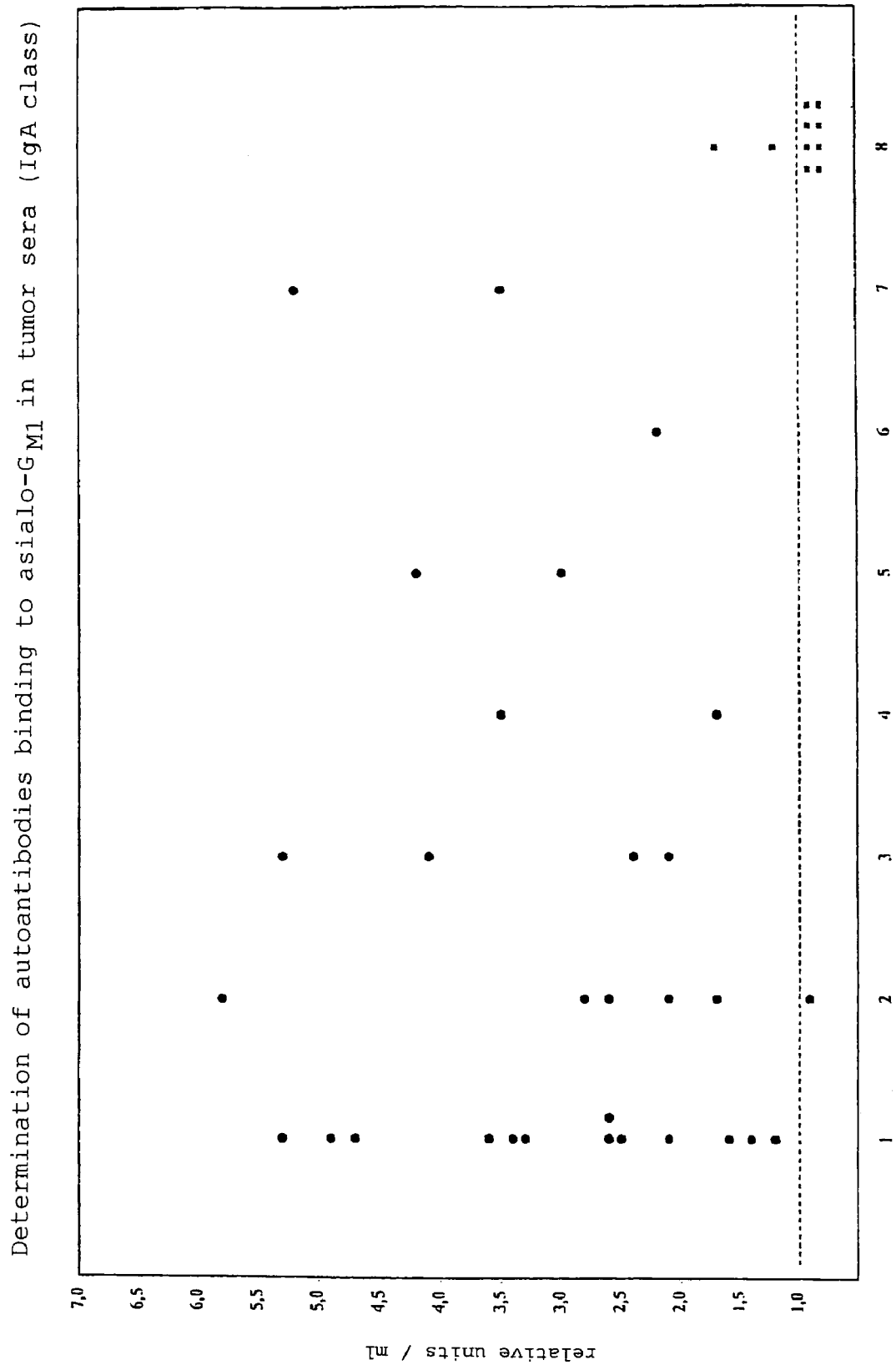
FIG. 8 shows a classification of the measurement of antibodies of the IgA class according to FIG. 4, corresponding to the classification of FIG. 5.

FIGS. 7 and 8 show the classifications, corresponding to FIGS. 5 and 6, of the results obtained with $AG_{M1}$-coated GA-CTs for the measured partial groups according to FIGS. 3 and 4. In FIGS. 7 and 8, the index numbers represent the following diagnoses:

| Index number | Diagnosis | Number of sera |
|---|---|---|
| 1 | Carcinoma of the colon | n = 13 |
| 2 | Carcinoma of the breast | m = 6 |
| 3 | Carcinoma of the pancreas | n = 4 |
| 4 | Carcinoma of the oesophagus | n = 2 |
| 5 | Carcinoma of the gall bladder | n = 2 |
| 6 | Carcinoma of the lung | n = 1 |
| 7 | Other | n = 2 |
|  | Epigastric tumour | n = 1 |
|  | Carcinoma of the appendix | n = 1 |
| 8 | Crohn's disease/ulcerative colitis | n = 10 |

Table 2 below summarizes the results of FIGS. 7 and 8 numerically.

| Organ affected | anti-$AG_{M1}$ IgG | anti-$AG_{M1}$ IgA | n |
|---|---|---|---|
| Colon/Rectum | 12 = 92% | 13 = 100% | 13 |
| Breast | 6 = 100% | 5 = 83% | 6 |
| Pancreas | 4 = 100% | 4 = 100% | 4 |
| Oesophagus | 2 = 100% | 2 = 100% | 2 |
| Gall bladder | 2 = 100% | 2 = 100% | 2 |
| Liver | 1 = 100% | 1 = 100% | 1 |
| Lung/bronchia | 1 = 100% | 1 = 100% | 1 |
| Other | 2 = 100% | 2 = 100% | 2 |

If a quantitative correlation of the measured results for the IgG determination which were obtained on the one hand with $G_{M1}$-coated test tubes and on the other hand, for the same partial group of sera, with $AG_{M1}$-coated test tubes is carried out, it is found, as shown in FIG. 9, that there is substantial agreement, which allows the conclusion that at least very substantially identical antibodies were measured in the two determinations.

The same applies to the IgA determinations, correlation corresponding to FIG. 9 being shown in FIG. 10.

4. Discussion of the Findings of the Determination of Anti-Ganglioside Antibodies in Control Sera and in Sera of Cancer Patients As expressly shown by the measured results summarized in FIGS. 1 to 10 and the above Tables 1 and 2, the determination of antibodies which bind to gangliosides ($AG_{M1}$ and/or $G_{M1}$) permits a clear distinction between the two groups of sera measured. The sensitivity of the determinations carried out was above 75% for all tumour types and in most cases even 100%. It therefore appears that the determinations of IgA using $AG_{M1}$-coated test tubes give measured results having the highest sensitivity (although as a limiting factor it is necessary to take into account that the number of determinations was smaller than in the case of the use of $G_{M1}$-coated test tubes).

It should furthermore be pointed out that, in an experiment, corresponding to the determinations of antibodies of the IgG and IgA type, also to determine those of the IgM type, no diagnostically relevant results were obtained (results not shown).

The measured high sensitivity in combination with a high unspecificity with respect to the various cancer types make the determination of anti-ganglioside antibodies, in particular of those of the IgG and/or IgA classes, a promising assay method for the diagnosis, in particular for the early diagnosis, of neoplasms.

The scientific literature does not reveal any discoveries which might suggest such a method. Only a few papers were known in which an attempt was made also to determine anti-ganglioside antibodies in connection with cancer diseases. Starting from the finding that increased/abnormal expression of gangliosides was found in the lung tissue of patients with "small cell lung cancer" (SCLC), two papers (58, 59) investigated whether this abnormal ganglioside expression makes it possible for anti-ganglioside antibodies to be formed and to be detected in cancer patients. In (58), the anti-fucosyl-$G_{M1}$-ganglioside antibodies sought were not found, while in (59), for the case of differentiated thyroid cancer (DTC), small amounts of different anti-ganglioside antibodies were detectable in a certain number of patients but, for example in the case of the anti-$G_{M1}$ antibody assay, the values found for the cancer patients were below those of the controls (FIG. 1). Slightly more greatly increased antibody titres were found only with respect to binding to the fucosylated ganglioside FucGM1. In the light of the findings described in the present Application, which clearly contradicts those according to (58, 59), it is to be assumed that, in view of the considerable practical difficulties in the determination of anti-ganglioside antibodies against an intense, serum-dependent background signal by means of the ELISA assay used by them, the authors of (58, 59) were not able actually to produce informative measured results. (58, 59) thus represent prior art clearly leading away from the method according to the invention.

A determination of various types of antibodies in sera of patients suffering from stomach cancer is furthermore described in (60), and a possible prognostic role of such a determination is discussed, "prognostic" being used in the context of a prognosis for the further clinical course of an existing and diagnosed cancer disease. An ELISA assay is used for the antibody determination. The antibodies which were found at increased levels compared with controls also include so-called anti-$G_{M1}$ antibodies, which however were found only with a sensitivity of about 35% in persons suffering from the disease (compared with a value of 5% for normal persons). In the light of (60) and other papers by the authors of (60), these anti-ganglioside antibodies are only one of numerous types of autoantibodies investigated in connection with cancer, and absolutely no suitability of the determination of such antibodies for diagnosis, in particular early diagnosis, and for the determination of the risk to a patient for developing a malignant cancer disease can be derived from the data reported in (60). Such a perspective was obtained for the first time from the measured data which was obtained by the Applicant using his considerable experience in the assay area and was extremely surprising against the background of the prior art.

On the basis of its measured results and an additional intensive study of the literature, the Applicant is convinced that the anti-ganglioside (auto)antibody titres which are found at increased levels in cancer patients have a completely different significance than that which was, for example, the starting point of the considerations of the authors of (58, 59, 60): it is in fact known that the so-called "natural killer cells" (NK cells; cytotoxically active lymphocytes) have, on their surface, asialo-$G_{M1}$ structures to which anti-$AG_{M1}$ antibodies can specifically bind, which antibodies thus deactivate and destroy the NK cells. Active NK cells play an extremely important role in the human immune defence by, for example, killing all degenerated endogenous cells, for example cancer cells, which, owing to their degeneration, have lost the capability of inhibiting the NK cells which come into contact with them. An impairment (inhibition, destruction) of the normal NK cells, which eliminates the selective cytotoxic properties thereof, therefore means that cells which have degenerated in the course of the natural life processes, in particular of the tumour cell type, are no longer properly eliminated. Owing to the improved prospects of survival of such degenerated potential tumour cells, these can, when the function of the NK cells has been disturbed, remain in the body, divide without hindrance and develop into an actual tumour. It should be pointed out that, in the area of animal experiments which employ experimental animals in which an artificial cancer is induced, it is already customary to switch off the immune defence of the experimental animal by administering anti-$AG_{M1}$ antibodies in conjunction with a carcinogen or a tumour nucleus, so that the experimental cancer—desired in the animal model—can develop (3 to 13).

Once the production of anti-asialo-$G_{M1}$ antibodies has been initiated or greatly increased in a human individual, for example owing to bacterial exposure (for example, in infections with *Campylobacter jejuni* or *Helicobacter pylori*; cf. 44 to 54), there is a precondition for potential damage to the NK cells and hence to the immune defence, with the consequence of an increased risk that degenerated tumour cells can develop into a tumour. It is therefore to be assumed that the anti-$AG_{M1}$ antibody titres found at significantly increased levels in all cancer sera which were measured in the context of the above-mentioned determinations are a consequence of the presence of a neoplasm (tumour) to a lesser extent in the context of the known tumour markers but rather are a precondition of its genesis. In the course of the tumour development, and in conjunction with stimulated NK cell activity, a "build-up" of the antibody titres may then occur in certain circumstances.

Since the antibodies cross-reacting with gangliosides and the effect on the immune system which is required for the production thereof may already be present before the development of a tumour, the determination of anti-$AG_{M1}$ antibodies can thus be effected according to the invention also in the context of determining a disposition, i.e. determining a cancer risk marker. In this context, it may be advantageous to carry out such a determination after in vivo stimulation of the antibody formation using safe stimulants. In view of the IgA antibodies found at substantially increased levels, the determination can also be effected expressly with suitable assays in body secretions (e.g. saliva, mucous).

In this context, it is of considerable interest that, as shown in particular in FIGS. 5 to 8, increased titres of anti-$AG_{M1}$ antibodies are also found in some of the patients who suffer from a chronic inflammatory intestinal disease (Crohn's disease, ulcerative colitis). It is known that, for example in ulcerative colitis, there is an increased risk that intestinal cancer will develop later on in the patients. The risk is about 40%. The finding that this percentage value is of the order of magnitude of the values which are found in sera of patients with chronic inflammatory intestinal diseases (index number 14 in FIGS. 5 and 6; index number 8 in FIGS. 7 and 8) for increased anti-$AG_{M1}$ titres, i.e. a parallelism of statistical cancer risk and an occurrence of anti-$AG_{M1}$ antibodies in the sera of relevant patients is detectable, is a further finding supporting the above-mentioned assumptions.

The consequences for novel methods for the prevention, inhibition and therapy of cancer which arise from the findings described in this Application form the subject of a separate parallel patent application filed simultaneously with the present Application.

LIST OF REFERENCES 1. http://www.medicine-worldwide.de/krankheiten/krebs/-xxx.html, wherein /xxx is to be replaced by e.g. /allgemeines; /lungenkrebs; /brustkrebs; /prostatakrebs; /darmkrebs; /leukaemie; /corpuskarzinom;
2. Lothar Thomas (Herausgeber), Labor und Diagnose, 5. erw. Auflage, Kapitel 34: Tumormarker, S. 956-1019;
3. Hugh F. Pross et al., Role of Natural Killer Cells in Cancer, Nat Immun 1993; 12:279-292;
4. Lewis L. Lanier et al., Arousal and inhibition of human NK Cells, Immunological Reviews 1997, Vol. 155:145-154;
5. Yoichi Fuji et al., IgG Antibodies to AsialoGM1 Are More Sensitive than IgM Antibodies to Kill in vivo Natural Killer Cells and Prematured Cytotoxic T Lymphocytes of Mouse Spleen, Microbiol. Immunol. Vol. 34(6), 533-542, 1990;
6. Carmine M. Volpe et al., AsGM1+NK Cells Prevent Metastasis of Invading LD-MCA-38 Tumor Cells in the Nude Mouse, J Surg Res 84, 157-161 (1999);
7. Susan D. Wilson et al., Correlation of Suppressed Natural Killer Cell Activity with Altered Host Resistance Models in B6C3F1 Mice, Toxicology and Applied Pharmacology 177, 208-218 (2001);
8. H. Yoshino et al., Natural killer cell depletion by anti-asialo GM1 antiserum treatment enhances human hematopoietic stem cell engraftment in NOD/Shi-scid mice; Bone Marrow Transplantation (2000) 26, 1211-1216;
9. N. Saijo et al., Analysis of Metastatic Spread and Growth of Tumor Cells in Mice with Depressed Natural Killer Activity by Anti-asialo GM1 Antibody or Anticancer Agents, J Cancer Res Clin Oncol (1984) 107: 157-163;
10. Sonoku HABU et al., Role of Natural Killer Cells against Tumor growth in Nude Mice—A Brief Review, Tokai J Exp Clin Med., Vol. 8, No. 5, 6: 465-468, 1983;
11. Lewis L. Lanier, NK Cell Receptors, Annu. Rev. Immunol. 1998, 16: 359-93;
12. Theresa L. Whiteside et al., The role of natural killer celss in immune surveillance of cancer; Current Opinion in Immunology 1995, 7:704-710;
13. Tuomo Timonen et al., Natural killer cell-target cell interactions, Current Opinion in Cell Biology 1997, 9:667-673;
14. Jose Abad Rodriguez et al., Plasma Membrane Ganglioside Sialidase Regulates Axonal Growth and Regeneration in Hippocampal Neurons in Culture, J Neurosci 21(21): 8387-8395, (2001);
15. Lindsey A. Miles et al., Gangliosides Interact Directly with Plasminogen and Urokinase and May Mediate Binding of These Fibrinolytic Components to Cells, Biochemistry 1989, 28, 9337-9343;
16. Haruyuki Qshima et al., Gangliosides can activate human alternative complement pathway, International Immunology, Vol. 5, No. 10, 1349-1351 (1993);
17. I. M. Dozmorov et al., Nanomolar Concentrations of Gangliosides Stimulate Primary Humoral Response, Biochemistry and Molecular Biology International, Vol. 42, No. 1:57-63 (1997);
18. John L. Ryan et al., Possible role for glycosphingolipids in the control of immune responses, Eur. J. Immunol. 1979, 9:171-175;
19. Robert W. Ledeen et al., The Role of GM1 and Other Gangliosides in Neuronal Differentiation, Annals New York Academy of Sciences, 1998, 161-175;
20. Sen-itiroh Hakomori et al., Functional Role of Glycosphingolipids in Cell Recognition and Signaling, J. Biochem. 118, 1091-1103 (1995);
21. Allan J. Yates et al., Ganglioside modulation of the PDGF receptor, Journal of Neuro-Oncology, 24, 65-73, 1995;
22. Anup K. Singh et al., Gangliosides as Receptors for Biological Toxins: Development of Sensitive Fluoroimmunoassays Using Ganglioside-Bearing Liposomes, Analytical Chemistry, Vol. 72, No. 24:6019-6024 (2000);
23. Howard C. Krivan et al., Many pulmonary pathogenic bacteria bind specifically to the carbohydrate sequence GalNAcβ1-4Gal found in some glycolipids, Proc. Natl. Acad. Sci. USA, Vol. 85:6157-6161 (1988);
24. Maim Bäackström et al., Characterization of an internal permissive site in the cholera toxin B-subunit and insertion of epitopes from human immunodeficiency virus-1, hepatitis B virus and enterotoxigenic *Escherichia coli*, Gene, 165 (1993) 163-171;
25. Wayne I. Lencer et al., Membrane traffic and the cellular uptake of cholera toxin, Biochimica et Biophysica Acta 1450 (1999) 177-190;
26. Adam J. Ratner et al., Cystic Fibrosis Pathogens Activate $Ca^{2+}$-dependent Mitogen-activated Protein Kinase Signaling Pathways in Airway Epithelial Cells, J. Biol. Chem. Vol. 276, No. 22, 19267-19275 (2001);
27. Richard H. Quarles et al., Autoantibodies Associated with Peripheral Neuropathy, Muscle Nerve, July 1999, 800-822;
28. Isoardo G et al., Anti-GM1 and anti-sulfatide antibodies in polyneuropathies, Acta Neurol Scand 2001:103: 180-187;
29. Rayomand Press et al., Temporal profile of anti-ganglioside antibodies and their relation to clinical parameters and treatment in Guillain-Barré syndrome, J Neurol Sci 190 (2001) 41-47;
30. Eduardo Nobile-Orazio, Multifocal motor neuropathy, J. Neuroimmunol. 115 (2001) 4-18;
31. Angelo Quattrini MD et al., Human IgM anti-GM1 autoantibodies modulate intracellular calcium homeostasis in neuroblastoma cells; J. Neuroimmunol. 114 (2001) 213-219;
32. Edith Uetz-von Almen et al., Antiganglioside GM1 Antibodies and Their Complement Activating Capacity in Central and Peripheral Nervous System Disorders and in Controls, Eur Neurol 1998; 39:103-110;
33. Noboyuki Hirota et al., The physiologial effect of anti-GM1 antibodies on saltatory conduction and transmembrane currents in single motor axons, Brain (1997) 120, 2159-2169;
34. Amjad A. Ilyas et al., Anti-$G_{M1}$ IgA antibodies in Guillain-Barré syndrome, J. Neuroimmunol., 36 (1992) 69-76;
35. Andrew J. Kornberg, Anti-GM1 ganglioside antibodies: their role in the diagnosis and pathogenesis of immune-mediated motor neuropathies, J. Clin. Neurosci. (2000) 7(3), 191-194;
36. A. S. Bansal et al., IgM ganglioside GM1 antibodies in patients with autoimmune disease or neuropathy, and controls, J. Clin. Pathol. 1994; 47:300-302;
37. Carmen Garcia Guijo et al., Presence and isotype of anti-ganglioside antibodies in healthy persons, motor neuron disease, peripheral neuropathy, and other diseases of the nervous system; J. Neuroimmunol. 56 (1995), 27-33;
38. Florina P. Thomas, Antibodies to GM1 and Gal(β1-3)Gal-Nac at the Nodes of Ranvier in Human and Experimental Autoimmune Neuropathy, Microscopy Research and Technique 34:536-543 (1996);

39. B. Gatterbauer et al., Antiglycosphingolipid Immune Responses in Neurology, Annals New York Academy of Sciences, 353-362;
40. H. J. Willison et al., Antiglycolipid antibodies, immunoglobulins and paraproteins in motor neuron disease: a population based case-control study; J. Neurol. Sci., 114 (1993) 209-215;
41. Chowdury D, et al., Axonal Guillain-Barré syndrome: a critical review, Acta Neurol Scand 2001: 103:267-277;
42. Joab Chapman et al., Antibodies to ganglioside $GM_1$ in patients with Alzheimer's disease, Neurosci. Lett. 86 (1988) 235-240;
43. D. Adams et al., Predictive value of anti-$GM_1$ gangliosi- de antibodies in neuromuscular diseases: a study of 180 sera; J. Neuroimmunol., 32 (1991) 223-230;
44. Nobuhiro Yuki et al., Cross-reactive antigen between nervous tissue and a bacterium elicits Guillain-Barré syndrome: Molecular mimicry between ganglioside $G_{M1}$ and lipopolysaccharide from Penner's serotype 19 of *Campylobacter jejuni*, Biomedical Research 13 (6) 451-453 (1992)
45. B. Schwerer et al., Antibody cross-reactivities between gangliosides and lipopolysaccharides of *Campylobacter jejuni* serotypes associated with Guillain-Barré syndrome, J. Endotox. Res. (1995) 2, 395-403;
46. Marina Bersudsky et al., Lipopolysaccharides of a *Campyiobacter coli* isolate from a patient with Guillain-Barré syndrome display ganglioside mimicry, Neuromuscular Disorders 10 (2000) 182-186;
47. Martina M. Prendergast et al., Lipopolysaccharides in the development of the Guillain-Barré syndrome and Miller Fisher syndrome forms of acute inflammatory peripheral neuropathies, J. Endotox. Res., Vol. 6, No. 5, 2000, 341-359;
48. Andrea Neisser et al., Serum Antibodies against Gangliosides and *Campylobacter jejuni* Lipopolysaccharides in Miller Fisher Syndrome, Infect. Immun. 65:4038-4042 (1997);
49. Michiaki Koga et al., Close association of IgA anti-ganglioside antibodies with antecedent *Campylobacter jejuni* infection in Guillain-Barré und Fisher's syndromes, J. Neuroimmunol. 81 (1998) 138-143;
50. Michiaki Koga et al., Subclass distribution and the secretory component of serum IgA anti-ganglioside antibodies in Guillain-Barré syndrome after *Campylobacter jejuni* enteritis, J. Neuroimmunol. 96 (1999) 245-250;
51. M. Mori et al., *Haemophilus influenzae* infection and Guillain-Barré syndrome, Brain (2000), 123, 2171-2178;
52. Yoram Nevo et al., Acute Immune Polyneuropathies: Correlations of Serum Antibodies to *Campylobacter jejuni* and *Helicobacter pylon* with Anti-$GM_1$ Antibodies and Clinical Patterns of Disease, J. Infect. Dis. 1997; 176 (Suppl. 2) S154-6;
53. T. McAlarney et al., Specifity and Cross-Reactivity of Anti-Galactocerebroside Antibodies, Immunol. Invest., 24(4), 595-606 (1995);
54. C. W. Ang et al., Guillain-Barré Syndrome- and Miller Fisher Syndrome-Associated *Campylobacter jejuni* Lipopolysaccharides Induce Anti-$GM_1$ and Anti-$GQ_{1b}$ Antibodies in Rabbits, Infect. Immun. Vol. 69, No. 4:2462-2469 (2001);
55. Steven Petratos et al., Antibodies against peripheral myelin glycolipids in people with HIV infection, Immunol. Cell Biol (1998), 76, 535-541;
56. M. Gisslén et al., Cerebrospinal Fluid Antibodies Directed against Neuron-Associated Gangliosides in HIV-1 Infection, Infection 28, 2000, No. 3:143-148;
57. C. Müler et al., Characterization of Autoantibodies to Natural Killer Cells in HIV-Infected Patients, Scand. J. Immunol. 43, 583-592, 1996;
58. Grazyna Adler et al., Small cell lung cancer is not associated with the presence of anti-fucosyl-GM1 ganglioside autoantibodies reactive in immunoenzyrnatic test, Lung Cancer 34 (2001) 383-385;
59. Aleksandra Lewartowska et al., Ganglioside reactive antibodies of IgG and IgM class in sera of patients with differentiated thyroid cancer, Immunol. Lett. 80 (2002) 129-132;
60. Manousos M. Konstandoulakis et al., Autoantibodies in the Serum of Patients with Gastric Cancer: Their Prognostic Importance; Hybridoma, Vol. 17, No. 5, 1998, 431-435;
61. Olle Nilsson, Carbohydrate antigens in human lung carcinomas, APMIS Suppl. 27, vol. 100, 149-164, 1992;
62. Michael Weller et al., Ganglioside antibodies: a lack of diagnostic specifity and clinical utility? J Neurol (1992) 239:455-459;
63. P. A. McCombe et al., Results of testing for anti-GM1 antibodies, J. Clin. Neurosci. (2000) 7(3), 209-212;
64. Einar Bech et al., ELISA-Type Titertray Assay of IgM Anti-GM1 Autoantibodies, Clin. Chem. 40/7, 1331-1334 (1994);
65. Alan Pestronk, MD et al., Multifocal motor neuropathy: Serum IgM anti-GM1 ganglioside antibodies in most patients detected using covalent linkage of GM1 to ELISA plates, Neurology 1997; 49:1289-1292;
66. Mepur H. Ravindranath et al., Factors affecting the fine specifity and sensitivity of serum antiganglioside antibodies in ELISA, J. Immunol. Methods 169 (1994) 257-272;
67. Armin Alaedini et al., Detection of anti-GM1 Ganglioside Antibodies in Patients with Neuropathy by a Novel Latex Agglutination Assay, J. Immunoassay, 21(4), 377-386 (2000);
68. Armin Alaedini et al., Ganglioside Agglutination Immunoassay for Rapid Detection of Autoantibodies in Immune-Mediated Neuropathy, J. Clin. Lab. Anal. 15:96-99, 2001;

The invention claimed is:

1. A method for the early diagnosis of cancer in a patient, said method comprising determining the amount of anti-asialo$G_{M1}$ (A$G_{M1}$) antibodies of the IgG and/or IgA type in a biological sample from a patient in whom cancer is suspected wherein said cancer is selected from the group comprising a carcinoma of the colon, a carcinoma of the breast, an ovarian carcinoma, a carcinoma of the pancreas, a carcinoma of the oesophagus, a carcinoma of the gall bladder, a carcinoma of the liver, a C cell carcinoma, a carcinoma of the thyroid, a carcinoma of the prostate, a carcinoma of the lung, a carcinoma of the appendix, a carcinoma of the bladder, a cardiac carcinoma, a carcinoma of the distal oesophagus, a carcinoma of the floor of the mouth, and a carcinoma of the kidney, wherein increased amounts of said antibodies compared with normal persons indicates the presence of cancer.

2. The method of claim 1, wherein the method is carried out with the aid of an immunoassay of the sandwich type or the competitive type.

3. The method of claim 2, wherein the immunoassay uses a reagent labeled with a chemiluminescence molecule.

\* \* \* \* \*

UNITED STATES PATENT AND TRADEMARK OFFICE
CERTIFICATE OF CORRECTION

| | |
|---|---|
| PATENT NO. | : 7,622,262 B2 |
| APPLICATION NO. | : 10/512935 |
| DATED | : November 24, 2009 |
| INVENTOR(S) | : Andreas Bergmann |

It is certified that error appears in the above-identified patent and that said Letters Patent is hereby corrected as shown below:

The name of the Assignee, B.R.A.H.M.S Aktiegesellschaft should not have a period following the letter "S". Delete "B.R.A.H.M.S." and insert --B.R.A.H.M.S--

Signed and Sealed this

Ninth Day of February, 2010

David J. Kappos
*Director of the United States Patent and Trademark Office*